US007988998B2

(12) United States Patent
Lenaerts et al.

(10) Patent No.: US 7,988,998 B2
(45) Date of Patent: *Aug. 2, 2011

(54) SUSTAINED-RELEASE TRAMADOL FORMULATIONS WITH 24-HOUR EFFICACY

(75) Inventors: Vincent Lenaerts, Beaconsfield (CA); Patricia Laure Ouadji-Nijki, Montreal (CA); Jonathan Bacon, Montreal (CA); Rachid Ouzérourou, Montreal (CA); Sonia Gervais, Laval (CA); Miloud Rahmouni, Dollars-des Ormeaux (CA); Damon Smith, St-Laurent (CA)

(73) Assignees: Labopharm Inc., Quebec (CA); Labopharm Europe Limited, Dublin (IE); Labopharm (Barbados) Limited, Hastings, Christ Church (BB)

( * ) Notice: Subject to any disclaimer, the term of this patent is extended or adjusted under 35 U.S.C. 154(b) by 1028 days.

This patent is subject to a terminal disclaimer.

(21) Appl. No.: 11/112,008

(22) Filed: Apr. 22, 2005

(65) Prior Publication Data

US 2007/0003618 A1 Jan. 4, 2007
US 2009/0047345 A9 Feb. 19, 2009

Related U.S. Application Data

(63) Continuation of application No. PCT/CA03/01638, filed on Oct. 27, 2003.

(60) Provisional application No. 60/509,062, filed on Oct. 25, 2002, provisional application No. 60/510,378, filed on Oct. 10, 2003.

(51) Int. Cl.
*A61K 9/20* (2006.01)
*A61K 9/22* (2006.01)
*A61K 9/24* (2006.01)
*A61K 9/28* (2006.01)
*A61K 9/30* (2006.01)
*A61K 9/42* (2006.01)

(52) U.S. Cl. ........ 424/468; 424/464; 424/465; 424/472; 424/474; 424/475; 424/476

(58) Field of Classification Search .................. None
See application file for complete search history.

(56) References Cited

U.S. PATENT DOCUMENTS

| | | |
|---|---|---|
| 2,987,445 A | 6/1961 | Levesque |
| 3,087,860 A | 4/1963 | Endicott et al. |
| 3,336,200 A | 8/1967 | Krause et al. |
| 3,381,009 A | 4/1968 | Palazzo et al. |
| 3,652,589 A | 3/1972 | Flick |
| 4,131,675 A | 12/1978 | Silvestrini |
| 4,820,522 A | 4/1989 | Radebaugh et al. |
| 4,906,632 A | 3/1990 | Silvestrini et al. |
| 4,938,968 A | 7/1990 | Mehta |
| 4,968,509 A | 11/1990 | Radebaugh et al. |
| 5,004,613 A | 4/1991 | Radebaugh et al. |
| 5,133,974 A | 7/1992 | Paradissis et al. |
| 5,273,760 A | 12/1993 | Oshlack et al. |
| 5,286,493 A | 2/1994 | Oshlack et al. |
| 5,336,691 A | 8/1994 | Raffa et al. |
| 5,407,686 A | 4/1995 | Patel et al. |
| 5,414,129 A | 5/1995 | Cherkez et al. |
| 5,427,799 A | 6/1995 | Valentine et al. |
| 5,456,921 A | 10/1995 | Mateescu et al. |
| 5,478,577 A | 12/1995 | Sackler et al. |
| 5,520,931 A | 5/1996 | Persson et al. |
| 5,560,331 A | 10/1996 | Komatsu et al. |
| 5,562,924 A | 10/1996 | Perrier et al. |
| 5,580,578 A | 12/1996 | Oshlack et al. |
| 5,591,452 A | 1/1997 | Miller et al. |
| 5,595,762 A * | 1/1997 | Derrieu et al. ............... 424/490 |
| 5,601,842 A | 2/1997 | Bartholomaeus et al. |
| 5,603,956 A | 2/1997 | Mateescu et al. |
| 5,616,343 A | 4/1997 | Cartilier et al. |
| 5,639,476 A | 6/1997 | Oshlack et al. |
| 5,663,279 A | 9/1997 | Kuiper et al. |
| 5,672,360 A | 9/1997 | Sackler et al. |
| 5,672,755 A | 9/1997 | Lerman et al. |
| 5,681,585 A | 10/1997 | Oshlack et al. |
| 5,773,031 A | 6/1998 | Shah et al. |
| 5,776,492 A | 7/1998 | Betzing et al. |
| 5,780,057 A | 7/1998 | Conte et al. |
| 5,807,575 A | 9/1998 | Dumoulin et al. |
| 5,814,338 A | 9/1998 | Veronesi et al. |
| 5,843,480 A | 12/1998 | Miller et al. |
| 5,849,240 A | 12/1998 | Miller et al. |
| 5,874,620 A | 2/1999 | Lerman et al. |
| 5,877,351 A | 3/1999 | Anderson |
| 5,879,705 A | 3/1999 | Heafield et al. |
| 5,879,707 A | 3/1999 | Cartilier et al. |

(Continued)

FOREIGN PATENT DOCUMENTS

CA 970688 7/1975

(Continued)

OTHER PUBLICATIONS

Adler, L. et al., "A Comparison of Once-Daily Tramadol with Normal Release Tramadol in the Treatment of Pain in Osteoarthritis," The Journal of Rheumatology 2002, vol. 29, No. 10, pp. 2196-2199.
Bodalia et al., "A Comparison of the Pharmacokinetics, Clinical Efficacy, and Tolerability of Once-Daily Tramadol Tablets with Normal Release Tramadol Capsules," Journal of Pain and Symptom Management, vol. 25, No. 2, pp. 142-149 (2003).
Boureau, "Tramadol in Post-Herpetic Neuralgia: A Randomized, Double-Blind, Placebo-Controlled Trial," PAIN, Elsevier Sci Pub. 2003, vol. 104 (1/2):323-331.
Brooks et al., "Trazodone—A Comparison of Single Night-time and Divided Daily Dosage Regimens," Psychopharmacology 84:1-4 (1984).

(Continued)

Primary Examiner — S. Tran
(74) Attorney, Agent, or Firm — Goodwin Procter LLP

(57) ABSTRACT

A sustained-release tramadol formulation oral administration is provided which, upon initial administration of one dose, provides an analgesic effect within 2 hours, which analgesic effect continues for at least 24 hours after administration.

29 Claims, 7 Drawing Sheets

U.S. PATENT DOCUMENTS

| | | | |
|---|---|---|---|
| 5,885,615 | A | 3/1999 | Chouinard et al. |
| 5,891,471 | A | 4/1999 | Miller et al. |
| 5,958,459 | A | 9/1999 | Chasin et al. |
| 5,965,163 | A | 10/1999 | Miller et al. |
| 5,968,551 | A | 10/1999 | Oshlack et al. |
| 5,981,592 | A | 11/1999 | Wechter et al. |
| 6,103,261 | A | 8/2000 | Chasin et al. |
| 6,129,205 | A | 10/2000 | Ergenbright et al. |
| 6,129,933 | A | 10/2000 | Oshlack et al. |
| 6,143,322 | A | 11/2000 | Sackler et al. |
| 6,143,325 | A | 11/2000 | Dennis et al. |
| 6,143,328 | A | 11/2000 | Heafield et al. |
| 6,143,353 | A | 11/2000 | Oshlack et al. |
| 6,156,342 | A | 12/2000 | Sriwongjanya et al. |
| 6,156,343 | A | 12/2000 | Morita et al. |
| 6,162,467 | A | 12/2000 | Miller et al. |
| 6,190,591 | B1 | 2/2001 | van Lengerich |
| 6,210,714 | B1 | 4/2001 | Oshlack et al. |
| 6,211,229 | B1 | 4/2001 | Kavey |
| 6,214,331 | B1 | 4/2001 | Vanderhoff et al. |
| 6,228,875 | B1 | 5/2001 | Tsai et al. |
| 6,238,698 | B1 | 5/2001 | Cremer et al. |
| 6,245,357 | B1 | 6/2001 | Edgren et al. |
| 6,245,387 | B1 | 6/2001 | Hayden |
| 6,248,363 | B1 | 6/2001 | Patel et al. |
| 6,254,881 | B1 | 7/2001 | McNally et al. |
| 6,254,887 | B1 | 7/2001 | Miller et al. |
| 6,277,887 | B1 | 8/2001 | Young |
| 6,284,273 | B1 | 9/2001 | Lenaerts et al. |
| 6,294,195 | B1 | 9/2001 | Oshlack et al. |
| 6,306,438 | B1 | 10/2001 | Oshlack et al. |
| 6,316,031 | B1 | 11/2001 | Oshlack et al. |
| 6,326,027 | B1 | 12/2001 | Miller et al. |
| 6,326,404 | B1 | 12/2001 | Koegel et al. |
| 6,339,105 | B1 | 1/2002 | Kamin et al. |
| 6,372,255 | B1 | 4/2002 | Saslawski et al. |
| 6,387,404 | B2 | 5/2002 | Oshlack et al. |
| 6,399,096 | B1 | 6/2002 | Miller et al. |
| 6,419,957 | B1 | 7/2002 | Lenaerts et al. |
| 6,451,350 | B1 | 9/2002 | Bartholomaeus et al. |
| 6,569,463 | B2 | 5/2003 | Patel et al. |
| 6,572,885 | B2 | 6/2003 | Oshlack et al. |
| 6,576,260 | B2 | 6/2003 | Bartholomaeus et al. |
| 6,586,006 | B2 | 7/2003 | Roser et al. |
| 6,593,373 | B2 | 7/2003 | Koegel et al. |
| 6,607,748 | B1 * | 8/2003 | Lenaerts et al. ............. 424/464 |
| 6,632,640 | B1 | 10/2003 | Lee et al. |
| 6,635,279 | B2 | 10/2003 | Kolter et al. |
| 6,645,537 | B2 | 11/2003 | Sweeney et al. |
| 6,659,373 | B1 | 12/2003 | Heren et al. |
| 6,660,774 | B2 | 12/2003 | Christoph et al. |
| 6,685,964 | B1 | 2/2004 | Bartholomaeus et al. |
| 6,723,343 | B2 | 4/2004 | Kugelmann et al. |
| 6,733,783 | B2 | 5/2004 | Oshlack et al. |
| 6,743,442 | B2 | 6/2004 | Oshlack et al. |
| 6,806,293 | B1 | 10/2004 | Zamir et al. |
| 6,806,294 | B2 | 10/2004 | Wimmer et al. |
| 6,863,901 | B2 | 3/2005 | Hirsh et al. |
| 6,923,988 | B2 | 8/2005 | Patel et al. |
| 6,962,717 | B1 | 11/2005 | Huber et al. |
| 6,968,551 | B2 | 11/2005 | Hediger et al. |
| 7,074,430 | B2 * | 7/2006 | Miller et al. ................. 424/468 |
| RE39,221 | E | 8/2006 | Raffa et al. |
| 7,083,807 | B2 | 8/2006 | Fanara et al. |
| 7,413,749 | B2 | 8/2008 | Wright et al. |
| 2001/0019725 | A1 | 9/2001 | Miller et al. |
| 2001/0036477 | A1 | 11/2001 | Miller et al. |
| 2001/0038852 | A1 | 11/2001 | Kolter et al. |
| 2002/0008133 | A1 | 1/2002 | Imasaki et al. |
| 2002/0012701 | A1 | 1/2002 | Kolter et al. |
| 2002/0032239 | A1 | 3/2002 | Koegel et al. |
| 2002/0044966 | A1 | 4/2002 | Bartholomaeus et al. |
| 2002/0055544 | A1 | 5/2002 | Kamin et al. |
| 2002/0106408 | A1 | 8/2002 | Bacon et al. |
| 2002/0165246 | A1 | 11/2002 | Holman |
| 2002/0176888 | A1 | 11/2002 | Bartholomaeus et al. |
| 2003/0021846 | A1 | 1/2003 | Kolter et al. |
| 2003/0035835 | A1 * | 2/2003 | Bartholomaeus et al. .... 424/468 |
| 2003/0044464 | A1 | 3/2003 | Ziegler et al. |
| 2003/0054032 | A1 | 3/2003 | Oshlack et al. |
| 2003/0069314 | A1 | 4/2003 | Christoph et al. |
| 2003/0092724 | A1 | 5/2003 | Kao et al. |
| 2003/0104061 | A1 | 6/2003 | Bartholomaeus et al. |
| 2003/0143270 | A1 | 7/2003 | Deboeck et al. |
| 2003/0148992 | A1 * | 8/2003 | Block et al. ..................... 514/52 |
| 2003/0152627 | A1 | 8/2003 | Beckert et al. |
| 2003/0158242 | A1 | 8/2003 | Kugelmann |
| 2003/0180362 | A1 | 9/2003 | Park et al. |
| 2004/0131671 | A1 | 7/2004 | Zhang et al. |
| 2004/0136924 | A1 | 7/2004 | Boyd et al. |
| 2004/0202716 | A1 | 10/2004 | Chan et al. |
| 2004/0259956 | A1 | 12/2004 | Wright et al. |
| 2005/0003002 | A1 | 1/2005 | Ziegler et al. |
| 2005/0157382 | A1 | 7/2005 | Kafka et al. |
| 2005/0256131 | A1 | 11/2005 | Coester |
| 2005/0276852 | A1 | 12/2005 | Davis et al. |
| 2006/0111307 | A1 | 5/2006 | Robbins |
| 2006/0172006 | A1 | 8/2006 | Lenaerts et al. |
| 2006/0240107 | A1 | 10/2006 | Lenaerts et al. |
| 2006/0269603 | A1 | 11/2006 | Brown Miller et al. |
| 2007/0048376 | A1 | 3/2007 | Baichwal et al. |
| 2007/0128269 | A1 | 6/2007 | Gervais et al. |
| 2007/0128275 | A1 | 6/2007 | Gervais et al. |
| 2007/0237816 | A1 | 10/2007 | Finkelstein |
| 2009/0047345 | A9 | 2/2009 | Lenaerts et al. |

FOREIGN PATENT DOCUMENTS

| | | |
|---|---|---|
| CA | 2140032 | 2/1994 |
| CA | 2280534 | 8/1998 |
| CA | 2321461 | 9/1999 |
| CA | 2295469 | 7/2000 |
| CA | 2414349 | 1/2002 |
| CA | 2433668 | 6/2002 |
| CA | 2466032 | 5/2003 |
| CA | 2503155 | 5/2004 |
| CA | 2503361 | 5/2004 |
| CA | 2489855 | 4/2005 |
| CL | 172000 | 10/2000 |
| DE | 4315525 | 11/1994 |
| DE | 4329794 | 3/1995 |
| DE | 19530575 | 2/1997 |
| DE | 19901683 | 7/2000 |
| DE | 19901687 | 7/2000 |
| DE | 19940740.1 | 3/2001 |
| DE | 19940944.7 | 3/2001 |
| DE | 10023699.5 | 4/2001 |
| DE | 19947747 | 4/2001 |
| DE | 19901686 | 6/2006 |
| EP | 0 566 709 | 10/1993 |
| EP | 0 624 366 | 11/1994 |
| EP | 0624366 | 11/1994 |
| EP | 0636370 | 2/1995 |
| EP | 0 642 788 | 3/1995 |
| EP | 0654263 | 5/1995 |
| EP | 0699436 | 3/1996 |
| EP | 0 729 751 | 9/1996 |
| EP | 0759296 | 2/1997 |
| EP | 0 864 325 | 9/1998 |
| EP | 1020183 | 7/2000 |
| EP | 1020185 | 7/2000 |
| EP | 1020186 | 7/2000 |
| EP | 1 138 320 | 10/2001 |
| EP | 1 190 712 | 3/2002 |
| EP | 1207866 | 5/2002 |
| EP | 1207867 | 5/2002 |
| EP | 1207868 | 5/2002 |
| EP | 1217998 | 7/2002 |
| EP | 1 468 679 | 10/2004 |
| EP | 1 527 775 | 5/2005 |
| EP | 1627633 | 2/2006 |
| GB | 2284760 | 6/1995 |
| NZ | 333401 | 10/1999 |
| WO | WO-0124783 | 1/1970 |
| WO | WO-94/02121 | 2/1994 |
| WO | WO-98/40053 | 9/1998 |
| WO | WO-99/01111 | 1/1999 |
| WO | WO-00/25769 | 5/2000 |

| WO | WO-00/32558 | 6/2000 |
| WO | WO-0041681 | 7/2000 |
| WO | WO-01/15667 | 3/2001 |
| WO | WO-01/15683 | 3/2001 |
| WO | WO-0115681 | 3/2001 |
| WO | WO-0115682 | 3/2001 |
| WO | WO-01/45676 | 6/2001 |
| WO | WO-02/02084 A1 | 1/2002 |
| WO | WO 0202084 A1 * | 1/2002 |
| WO | WO-02/060415 | 8/2002 |
| WO | WO-03/037296 | 5/2003 |
| WO | WO-03/072025 | 9/2003 |
| WO | WO-03/080031 | 10/2003 |
| WO | WO-2004003722 | 1/2004 |
| WO | WO-2004038428 A2 | 5/2004 |
| WO | WO-2004/080447 | 9/2004 |

OTHER PUBLICATIONS

Desmeules, "The tramadol option," European Journal of Pain, 4, Suppl. A:15-21 (2000).
Fabre, "Trazodone Dosing Regimen: Experience with Single Daily Administration," J. Clin. Psychiatry 51:9 (suppl.), pp. 23-26 (1990).
Fleischmann, "Tramadol for the treatment of joint pain associated with osteoarthritis: a randomized, double-blind, placebo-controlled trial," Current Therapeutic Research 62(2):113-128 (2001).
Haria et al., "Trazodone: A Review of its Pharmacology, Therapeutic Use in Depression and Therapeutic Potential in Other Disorders," Drugs & Aging 4(4):331-355 (1994).
International Search Report for International Patent Application No. PCT/CA03/01637, dated Apr. 27, 2004.
International Search Report for International Patent Application No. PCT/CA03/01638, dated Apr. 27, 2004.
Kasper et al., "A Comparative, Randomised, Double-Blind Study of Trazodone Prolonged-Release and Paroxetine in the Treatment of Patients with Major Depressive Disorder," Current Med. Res. & Opinion vol. 21 No. 8, pp. 1139-1146 (2005).
Klaschik, "Office-oriented pain therapy in cancer patients—Adequate alleviation of pain with the appropriate medication," Klinikarzt 31(9):250-256 (2002). (English abstract provided on p. 256).
Mateescu, "Use of Crosslinked Amylose for the Quantitative Determination of α- and β-Amylase," Lab. Enzymol., Inst. Sci. Biol., Bucharest, Rom., Biochimie 60(5), 535-7 (1978) (English Abstract provided).
Mendelson, "A Review of the Evidence for the Efficacy and Safety of Trazodone in Insomnia," J. Clin. Psychiatry 66:4, pp. 469-476 (2005).
Moon et al., "Efficacy and Tolerability of Controlled-Release Trazodone in Depression: A Large Multi-Centre Study in General Practice," Current Med. Res. and Opinion vol. 12, No. 3, pp. 160-168 (1990).
Partial European Search Report for EP 04 02 4164, Aug. 9, 2006.
Ruoff, "Slowing the initial titration rate of tramadol improves tolerability," Pharmacotherapy 19(1):88-93 (Jan. 1999).
Saletu-Zyhlarz et al., "Confirmation of the Neurophysiologically Predicted Therapeutic Effects of Trazodone on Its Target Symptoms Depression, Anxiety and Insomnia by Postmarketing Clinical Studies with a Controlled-Release Formulation in Depressed Outpatients," Neuropsychobiology 2003; 48:194-208.
Search Report and Written Opinion for Intl. Application PCT/CA2006/001483, Jun. 4, 2007.
Search Report and Written Opinion for Intl. Application PCT/CA2006/001484, Jun. 8, 2007.
Stamer, "Impact of CYP2D6 genotype on postoperative tramadol analgesia," PAIN, 105(1-2):231-238 (2003).
Visavarungroj, N. et al., "Crosslinked Starch as a Disintegrating Agent," International Journal of Pharmaceutics 1990, vol. 62, No. 2/3, pp. 125-131.
Product Monograph for $^{Pr}$Zytram XL Tramadol Hydrochloride Controlled Release Tablets—150, 200, 300 and 400 mg Professed Standard Opioid Analgesic, dated Jul. 19, 2010 (32 pages).
Opposition statement against Chilean Application No. 600-2007 by Asociacion Industrial de Laboratorios Farmaceuticos AG (in Spanish) and an English translation.
Opposition statement against Chilean Application No. 605-2007 by Laboratorios Recalcine S.A. (in Spanish) and an English translation.
Gennaro R. Alfonso, Remington Farmacia, 19th Edition, Panamericana, Spain. 1988, pp. 2470, 2535 (in Spanish) and an English translation.
Nies and Spielberg, Goodman & Gilman. Las Bases Farmacologicas de la Terapeutica. Novena Edicion. vol. I. McGraw-Hill. Interamericana. Mexico. 1996, pp. 47, 58 (in Spanish) and an English translation.
Opposition statement against Chilean Application No. 605-2007 by Asociacion Industrial de Laboratorios Farmaceuticos AG (in Spanish) and an English translation.
Labopharm, Inc. Press Release dated Feb. 2, 2010 relating to FDA approval of OLEPTRO™ (4 pages).

* cited by examiner

SUSTAINED-RELEASE TRAMADOL FORMULATIONS WITH 24-HOUR EFFICACY

CROSS-REFERENCE TO RELATED APPLICATIONS

This application is a continuation of International (PCT) Patent Application Serial No. PCT/CA2003/001638, filed Oct. 27, 2003, which claims priority to and the benefit under 35 U.S.C. §119(e) of U.S. Provisional Application Ser. No. 60/510,378, filed Oct. 10, 2003, and U.S. Provisional Application Ser. No. 60/509,062, filed Oct. 25, 2002.

FIELD OF THE INVENTION

This invention relates to a novel once daily oral pharmaceutical composition for controlled release of tramadol or a salt thereof.

BACKGROUND OF THE INVENTION

Tramadol Pharmaceutical Formulations

Tramadol hydrochloride (HCl) was developed by Grünenthal GmbH, Germany. It has been marketed in Germany since 1977 (eg. Tramal™), and in the United States as Ultram® since 1995. The efficacy and safety profile of tramadol HCl make it highly suitable as a long-term treatment for chronic pain.

Tramadol HCl is a synthetic, centrally acting analgesic that has been shown to be effective in a variety of acute and chronic pain states. In particular, tramadol HCl, in both immediate and slow-release formulations, in conjunction with non-steroidal anti-inflammatory drugs (NSAIDs) (Roth S H "Efficacy and safety of tramadol HCl in breakthrough musculoskeletal pain attributed to osteoarthritis". J. Rheumatol 1998; 25:1358-1363. Wilder-Smith C H et al. "Treatment of severe pain from osteoarthritis with slow-release tramadol or dihydrocodeine in combination with NSAID's: a randomized study comparing analgesia, antinociception and gastrointestinal effects". Pain 2001; 91:23-31.), has been demonstrated to reduce pain attributed to osteoarthritis (OA). After oral administration, tramadol HCl is rapidly and almost completely absorbed, and it is extensively metabolized. The major metabolic pathways appear to be N- and O-demethylation and glucuronidation or sulfonation in the liver. Only one metabolite, mono-O-desmethyltramadol (M1), is pharmacologically active, which has an approximate 200-fold higher affinity for the µ-opioid receptor than racemic tramadol (DeJong R. "Comment on the hypoalgesic effect of tramadol in relation to CYP2D6" (comment) Pain Dig 1997; 7:245; Kogel B. et al "Involvement of metabolites in the analgesic action of tramadol" Proc. 9$^{th}$ World Congress on Pain, Vienna, 1999). In healthy humans, tramadol is demethylated by the polymorphic enzyme cytochrome P450 2D6 (CYP2D6) to the M1 metabolite.

The mechanism of action of tramadol HCl is not completely understood. Animal models indicate that the drug (and its active M1 metabolite) acts as an opiate agonist, apparently by selective activity at the µ-receptor. In addition to opiate agonist activity, tramadol HCl inhibits re-uptake of certain monoamines (norepinephrine, serotonin) which appears to contribute to the drug's analgesic effect. The antinociceptic effect of tramadol HCl is only partially antagonized by naloxone in some tests in animals and humans. In addition, because of the drug's opiate agonist activity, it has been suggested that tramadol HCl may produce dependence; however, its abuse potential appears to be low, and tramadol HCl is not "subject to control" under the United States Federal Controlled Substances Act of 1970 as a scheduled drug.

Immediate release formulations of tramadol HCl are well known in the art. Such formulations, however, require frequent dosing in order to provide effective pain relief. Lack of compliance with high frequency dosing regimens can result in inconsistent plasma drug concentrations and accordingly less consistent analgesia. Twice daily formulations are available and are desirable over immediate release formulations as they provide longer periods of analgesia after administration and require less frequent dosing. A once daily formulation is even more desirable for increased effectiveness, safety and convenience.

A critical factor influencing the rate of absorption, and thereby the safety and efficacy, of an active pharmaceutical ingredient by the body following oral administration in a tablet or other solid dosage form is the rate of release of the active pharmaceutical ingredient from that dosage form post ingestion.

It is thus the ability of the dosage form components to control the release rate that constitutes the basis for the so-called controlled-release, extended-release, sustained-release or prolonged-action pharmaceutical preparations that are designed to produce slow, uniform release and absorption of active pharmaceutical ingredients over a period of hours, days, weeks or months. The advantages of such controlled-release formulations include: a reduction in the required administration frequency of the drug as compared to conventional immediate release dosage forms, often resulting in improved patient compliance; the maintenance of a stable concentration of the drug in the body and thereby a sustained therapeutic effect over a set period of time; and a decreased incidence and intensity of undesired side effects of the active agent caused by the high plasma concentrations that occur after administration of immediate-release dosage forms.

Many materials have been proposed and developed as matrices for the controlled release of active pharmaceutical ingredients. These include, for example, polymeric materials such as polyvinyl chloride, polyethylene amides, ethyl cellulose, silicone and poly(hydroxymethyl methacrylate). See e.g., U.S. Pat. No. 3,087,860 to Endicott et al; U.S. Pat. No. 2,987,445 to Levesque et al.; Salomon et al. Pharm. Acta Helv., 55, 174-182 (1980); Korsmeyer, Diffusion Controlled Systems: Hydrogels, Chap. 2, pp 15-37 in Polymers for Controlled Drug Delivery, Ed Tarcha, CRC Press, Boca Raton, Fla. USA (1991); and Buri et al., Pharm. Acta Helv. 55, 189-197 (1980).

High amylose starch has also been used for controlled-release purposes and, in particular, recent advances have been made using cross-linked high amylose starch. For example, U.S. Pat. No. 6,284,273 (Lenaerts et al.), which issued Sep. 4, 2001, and No. 6,419,957 (Lenaerts et al.), which issued Jul. 16, 2002, teach a solid controlled release oral pharmaceutical dosage unit in the form of tablets comprising a dry powder of a pharmaceutical product and a dry powder of cross-linked high amylose starch, wherein said cross-linked high amylose starch is a matrix comprising a mixture of about 10-60% by weight of amylopectin and about 40-90% amylose. U.S. Pat. No. 6,607,748 (Lenaerts et al.) which issued on Aug. 19, 2003 describes a process for making a cross-linked high amylose starch which is known under the name Contramid®.

Extended Release Formulations Known in the Art

Extended and controlled release formulations relating to tramadol HCl have been suggested, examples being described in: United States Patent Application Publication No. 2003/0143270, (Deboeck et al.) published Jul. 31, 2003; U.S. Pat. No. 6,254,887 (Miller et al.) issued Jul. 3, 2001;

United States Patent Application Publication No. 2001/0036477 (Miller et al.) published Nov. 1, 2001; U.S. Pat. No. 6,326,027 (Miller et al.) issued Dec. 4, 2001; and U.S. Pat. No. 5,591,452 (Miller et al) issued Jan. 7, 1997; and European Patent No. 1 190 712 (Vanderbist) published Mar. 27, 2002.

Although there are some controlled release tramadol HCl formulations on the market which purport to be once-daily formulations, none of these has successfully replaced twice-daily tramadol HCl formulations.

Articles have been published in which comparative data between putative "once-daily" tramadol HCl formulations and immediate release tramadol HCl formulations are presented. Adler et al., "A Comparison of Once-Daily Tramadol with Normal Release Tramadol in the Treatment of Pain in Osteoarthritis," The Journal of Rheumatology (2002) 29(10): 2195-2199; and Bodalia et al., "A Comparison of the Pharmacokinetics, Clinical Efficacy, and Tolerability of Once-Daily Tramadol Tablets with Normal Release Tramadol Capsules," Journal of Pain and Symptom Management (2003) 25(2): 142-149.

Adverse Events from Administration of Tramadol HCl

The most frequently reported side effects of tramadol observed in clinical trials in the United States are constipation, nausea, dizziness/vertigo, headache, somnolence and vomiting. These are typical adverse effects of opiate drugs. Seizures and anaphylactoid reactions have also been reported, though the estimated incidence of seizures in patients receiving tramadol HCl is less than 1% (Kazmierczak, R., and Coley, K.: "Doctor letters on prescribing: evaluation of the use of tramadol HCl." Formulary 32: 977-978, 1997).

Adler et al., supra, reports on the results of a clinical study comparing a once daily tramadol formulation to immediate release tramadol in the treatment of pain in osteoarthritis. The authors report similar adverse event profiles for individuals in both treatment groups. Table 2 of Adler et al. indicates that a greater percentage of people who were in the once daily treatment group withdrew due to adverse events than did those in the other treatment group.

In Bodalia et al., supra, the authors report comparable tolerability with a 150 mg once daily dose, a 200 mg once daily dose and three doses of a 50 mg normal release tramadol formulation. This article does not however include any information on how to make the formulations which are purported to be "once daily" nor does the article disclose any pharmacokinetic data after a single dose.

Citation or identification of any reference in this section shall not be construed as an admission that such reference is available as prior art to the present invention.

SUMMARY OF THE INVENTION

An object of the present invention is to provide an improved sustained-release tramadol formulation with 24-hour effective analgesia.

In accordance with one aspect of the present invention, there is provided a once daily oral pharmaceutical composition for controlled release of tramadol or a salt thereof, in which the composition, upon initial administration, provides an onset of analgesic effect within 2 hours, which analgesic effect continues for at least 24 hours after administration.

In accordance with another aspect of the present invention, there is provided a once daily oral pharmaceutical composition for controlled release of tramadol or a salt thereof, wherein the composition, upon initial administration of one dose, provides a mean plasma concentration of at least 100 ng/mL within 2 hours of administration and continues to provide a mean plasma concentration of at least 100 ng/mL for at least 22 hours after administration.

In an embodiment of the present invention, there is provided a once daily oral pharmaceutical composition for controlled release of tramadol or a salt thereof, wherein the composition, upon initial administration of one dose, provides a mean plasma concentration of at least 100 ng/mL within 2 hours of administration and continues to provide a mean plasma concentration of at least 100 ng/mL for at least 22 hours after administration and wherein the mean maximum plasma concentration ($C_{max}$) is less than 2.2 times the mean plasma concentration obtained 24 hours after administration ($C_{24h}$).

The term "$\lambda_z$" is the apparent terminal elimination rate constant, determined by the slope of the regression during the log-linear phase.

The term "$AUC_{0-Tmax}$" is the mean area under the plasma concentration-time curve from time 0 to $T_{max}$ and is used as an indicator of the rate of drug absorption, or metabolite formation. It is calculated as the arithmetic mean of the area under the plasma concentration-time curve from time 0 to $T_{max}$ calculated for each individual participating in the bioavailability study.

The term "$AUC_{0-\infty}$" is the mean area under the plasma concentration-time curve extrapolated to infinity It is calculated as the arithmetic mean of the area under the plasma concentration-time curve from time 0 extrapolated to infinity, calculated for each individual participating in the bioavailability study.

The term "analgesic effect" is defined for the purposes of the present invention as providing a mean blood plasma concentration of at least about 100 ng/mL of tramadol.

The term "$C'_{max}$" is the maximum observed plasma concentration, calculated as the mean of the individual maximum blood plasma concentrations.

The term "controlled release" is defined for purposes of the present invention as a method of oral drug delivery where the rate of release of the active pharmaceutical ingredient from the formulation is not solely dependent on the concentration of active pharmaceutical ingredient remaining in the formulation and/or the solubility of the active pharmaceutical ingredient in the medium surrounding the formulation, and where the time course and/or location of release of an active ingredient from a pharmaceutical formulation are chosen to accomplish therapeutic or convenience objectives not offered by conventional dosage forms.

The term "half-life" is the apparent terminal elimination half-life.

The term "HVD" is the half value duration, that is, the time during which tramadol concentrations are above one half the $C'_{max}$. This parameter is an indicator of the shape of the plasma concentration time curve.

The term "immediate release" is defined for purposes of the present invention as the release of an active ingredient from a pharmaceutical formulation where the rate of release of the active pharmaceutical ingredient from the pharmaceutical formulation is not retarded by means of a controlled release matrix and where the components of the pharmaceutical formulation are designed such that, upon ingestion, maximum exposure of said active pharmaceutical ingredient to body tissues occurs in the minimum period of time.

The term "initial administration" is defined for purposes of the present invention as the first single dose of a formulation containing an active ingredient administered to a patient or subject or the first dose administered to a patient or subject after a suitable washout period.

The term "MRT" is the mean residence time, which is an estimate of the average time that a tramadol molecule resides in the body following oral administration.

The term "mean maximum plasma concentration" ($C_{max}$) is defined for the purposes of the present invention as the maximum mean plasma concentration.

The term "mean plasma concentration" is defined for purposes of the present invention as the arithmetic mean blood plasma concentration. 0026a]

The term "$t_{max}$" is the time at which $C_{max}$ is achieved.

The term "$T_{max}$" is the time at which the maximum blood plasma concentration is observed for each individual participating in the bioavailability study.

The term "Rstart" is the time at which plasma concentrations begin to decline in a log-linear fashion, that is, the time at which either drug absorption or metabolite formation is complete.

The word "tramadol", as used herein shall refer to tramadol, its stereoisomers and its pharmaceutically acceptable salts.

The term "steady state" is defined for purposes of the present invention as the state, following multiple dose administration, where the rate of drug elimination matches the rate of input and the plasma drug concentrations at a given time within a dosing interval are approximately the same from one dosing interval to another.

BRIEF DESCRIPTION OF THE FIGURES

Various features and advantages of the present invention, will become clear from the more detailed description given below with reference to the accompanying drawings, in which.

DETAILED DESCRIPTION OF THE INVENTION

Core

Figure 1:
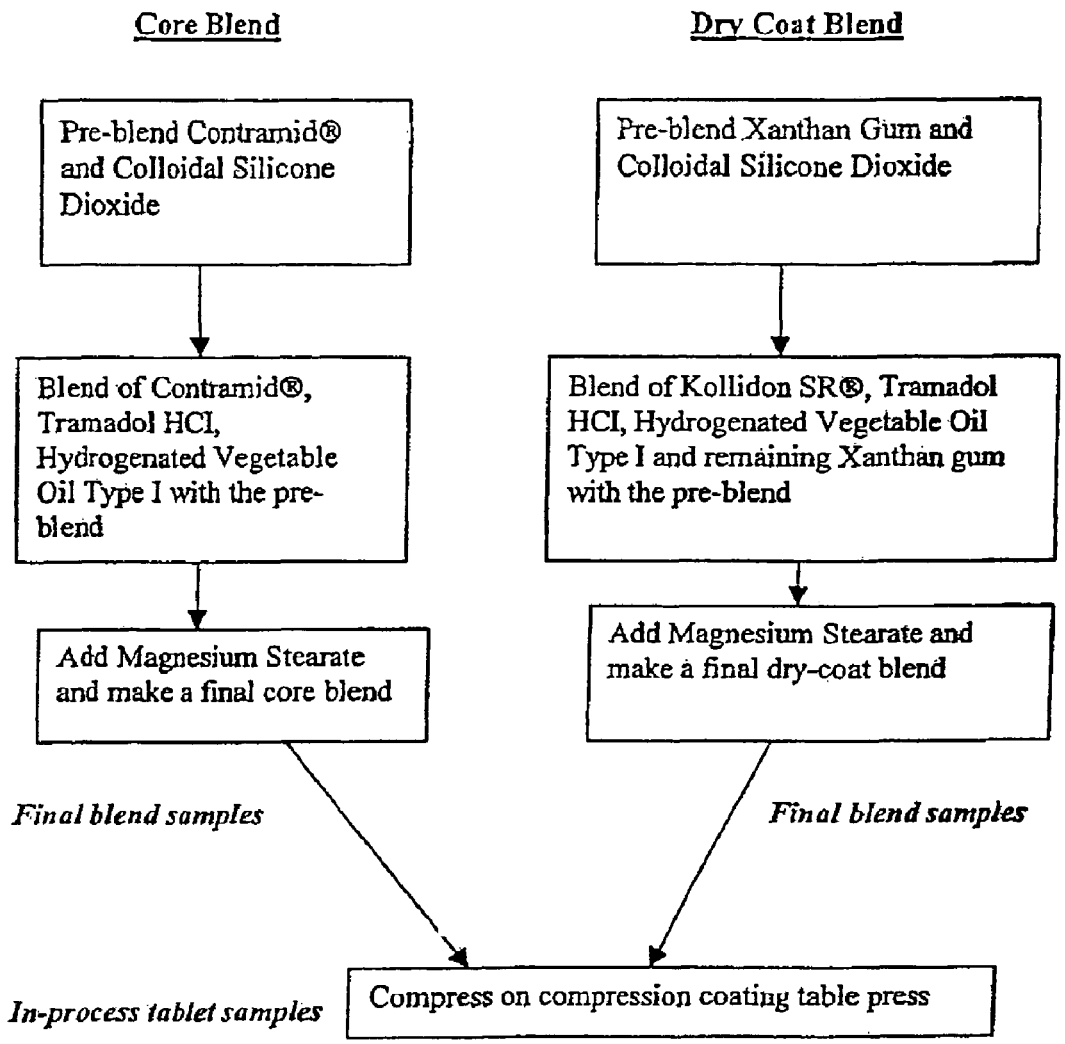
FIG. 1: Flow diagram showing manufacturing process for tablets.

The core of a tablet of the invention includes at least one active ingredient and a matrix, these components associated in such a way that release of the pharmaceutical ingredient from the matrix is controlled. In a specific embodiment, the matrix of the core is a cross-linked high amylose starch known under the name Contramid®, and described most recently in U.S. Pat. No. 6,607,748 (Lenaerts et al.), which issued Aug. 19, 2003. A preferred formulation in the context of this invention is provided in the specification of U.S. Pat. No. 6,607,748.

Preferably, the core is formed by admixing the ingredients (in granular or powder form) and then compressing the mixture to form the core over which the coat is subsequently formed. The weight of the core can be any percentage of the weight of the total composition between 10% and 80%. The preferred percentage depends, upon other things, the total dosage of the pharmaceutical agent. In a particular embodiment described further below, a tablet contains 100 mg tramadol hydrochloride and the core is about 26% of the total weight of the tablet. In another embodiment, a tablet contains 200 mg tramadol hydrochloride and the core makes up about 33% of the total weight of the tablet. In yet another embodiment, a tablet contains 300 mg tramadol hydrochloride, and the core contributes 33% to the total weight of the tablet.

Active Agent in the Core

An active pharmaceutical ingredient is present in the core of the composition of the present invention. A suitable pharmaceutical ingredient of the present invention is any such ingredient that is desired to be delivered in a sustained-release dosage form. A comprehensive list of suitable pharmaceutical agents can be found in *The Merck Index*, 12th Ed. Preferably, the pharmaceutical ingredient is, but not limited to, isonicotinic acid hydrazide, sodium salicylate, pseudoephedrine hydrochloride, pseudoephedrine sulfate, acetaminophen or diclofenac sodium, verapamil, glipizide, nifedipine, felodipine, betahistine, albuterol, acrivastine, omeprazole, misoprostol, Tramadol®, oxybutynin, trimebutine, ciprofloxacin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisal, naproxen, ketorolac, diclofenac, tolmetin, sulindac, phenacetin, piroxicam, mefamanic acid, dextromethorphan, other non-steroidal anti-inflammatory drugs including salicylates, pharmaceutically acceptable salts thereof or mixtures thereof. Prodrugs are part of the invention.

The solubility of the pharmaceutical agent in aqueous solution can be a wide variety of values. The aqueous solubility of the pharmaceutical agent can be less than $10^{-3}$ g/L, more than $10^{-3}$ g/L, more than $10^{-2}$ g/L, more than $10^{-1}$ g/L, more than 1 g/L, more than 10 g/L, more than 100 g/L, more than 500 g/L, more than 1000 g/L, or more than 2000 g/L. Preferably, the solubility is more than 100 g/L. More preferably, the solubility is more than 500 g/L. Most preferably, the solubility is more than 1000 g/L.

The pharmaceutical agent can meet a variety of dosage requirement. For example, the dosage requirement of the pharmaceutical agent can be less than 1 mg/dosage unit, more than 1 mg/dosage unit, more than 10 mg/dosage unit, more than 100 mg/dosage unit, more than 200 mg/dosage unit, more than 300 mg/dosage unit, more than 400 mg/dosage unit, more than 500 mg/dosage unit, or more than 1000 mg/dosage unit. Preferably, the pharmaceutical agent is more than 50 mg/dosage unit. More preferably, the pharmaceutical agent is 100 mg/dosage unit, or more, e.g. 150 mg/dosage unit, or 200 mg/dosage unit, or 250 mg/dosage unit, or 300 mg/dosage unit, or more.

Particular embodiments include a core containing tramadol hydrochloride in which the core contains between about 10% and 90% of the total tramadol present in the tablet, e.g. about 45 mg of a 100 mg strength tablet (45% of the tablet total), or about 90 of a 200 mg strength tablet (45% of the tablet total), or about 151 mg of a 300 mg strength tablet (50% of the tablet total).

Matrix of the Core

The release from the formulation of an active pharmaceutical ingredient located in the core is slower than the release of an active pharmaceutical ingredient located in the matrix of the coat. A preferred matrix of the core is cross-linked high amylose starch, known under the name Contramid® and described in U.S. Pat. No. 6,607,748. In particular embodiments, the matrix makes up between about 10% and about 90% by weight of the core i.e., the ratio of the matrix of the core to the active ingredient of the core (w/w) is between about 0.1 and about 10, or between about 0.2 and about 9, or between about 0.2 and about 8, or between about 0.3 and about 7, or between about 0.4 and about 6, or between about 0.5 and about 5, or between about 0.6 and about 4, or between about 0.7 and about 4 or between about 1 and about 4, or between about 1 and about 3 and about 1.5 and about 2.5. In one particular embodiment, the core totals about 90 mg, of which about 44 mg is Contramid®, and 45 mg is tramadol hydrochloride In this case, Contramid® thus makes up about 49 weight percent of the core.

Optional Components

The core composition of the present invention may optionally include a pharmaceutically acceptable carrier or vehicle. Such carriers or vehicles are known to those skilled in the art and are found, for example, in *Remingtons's Pharmaceutical Sciences,* 14$^{th}$ Ed. (1970). Examples of such carriers or vehicles include lactose, starch, dicalcium phosphate, calcium sulfate, kaolin, mannitol and powdered sugar. Additionally, when required, suitable binders, lubricants, and disintegrating agents can be included. If desired, dyes, as well as sweetening or flavoring agents can be included.

The core composition of the present invention may optionally include accessory ingredients including, but not limited to dispersing agents such as microcrystalline cellulose, starch, cross-linked starch, cross-linked poly(vinyl pyrrolidone), and sodium carboxymethyl cellulose; flavoring agents; coloring agents; binders; preservatives; surfactants and the like.

The core can, optionally, also include one or more suitable binders known to one of ordinary skilled in the art.

Suitable forms of microcrystalline cellulose, for example, MCC-PH101, MCC-102, MCC-105, etc.

Suitable lubricants, such as those known to the skilled person, may also be included. For example, magnesium stearate, vegetable oil, talc, sodium-stearyl fumarate, calcium stearate, stearic acid, etc.

Suitable glidants, known in the art, may also be included. Examples of such glidants include, but are not limited to talc, colloidal silicon dioxide, etc.

Proportion

The active agent is present at levels ranging from about 1 to about 90 wt. % of the total weight of the core, preferably from about 10 to about 70 wt. % of the total composition of the core, more preferably from about 20 to about 60 wt. % of the total composition of the core, and probably most often between about 30 to about 50 wt. % of the total composition of the core.

Of course, the total amount of all components is 100 wt. %, and those of ordinary skill in the art can vary the amounts within the stated ranges to achieve useful compositions.

Coat

The coat of the dosage form includes a physical mixture of polyvinyl acetate and polyvinylpyrrolidone and the active pharmaceutical ingredient(s) of the coat. The coat can also include a cross-linked high amylose starch, e.g., Contramid®, and other optional components. In a preferred embodiment, the coat is formed by dry compression. The weight of the coat can be any percentage of the weight of the total composition between about 10% and about 90%, but is preferably in the higher part of this range. The coat thus usually makes up between about 20% to about 90%, (w/w) of a tablet of the invention, or about 25% to about 90%, or about 30% to about 85%, or about 35% to about 85%, or about 40% to about 85%, or about 45% to about 85%, or about 45% to about 90%, or about 50% to about 90% or about 50% to about 85%, or about 55% to about 90%, or about 55% to about 85%, or about 55% to about 80%, or about 60% to about 90%, or about 60% to about 85%, or about 60% to about 80%, or about 60% to about 75%, or about 65% to about 90%, or about 65% to about 85%, or about 65% to about 80%, or about 65% to about 75%, or about 65% or about 70% or about 75%.

The coat often includes an optional binding agent.

Polyvinyl Acetate and Polyvinylpyrrolidone of the Coat

The weight percentage of the polyvinyl acetate/polyvinylpyrrolidone mixture in the coat can be anywhere within a wide range of values. Depending on the solubility in water of the active ingredient in the coat, the amount of the polyvinyl acetate/polyvinylpyrrolidone mixture in the coat can be adjusted. United States Patent Publication No. 2001/0038852 describes ways in which such adjustments can be made. For example, for active ingredients that are soluble to extremely soluble in water, polyvinyl acetate/polyvinylpyrrolidone mixture can be about 20 to about 80 wt. % of the coat, preferably about 30 to about 65 wt. %, or about 40 to about 55 wt. %. In a particular embodiment described below, Kollidon™ SR makes up about 45% by weight of a coat that is about 31% by weight tramadol hydrochloride and about 23% xanthan gum. For active ingredients that are sparingly soluble to slightly soluble in water, the amount of polyvinyl acetate/polyvinylpyrrolidone mixture is often lower, as described in United States Patent Publication No. 2001/0038852.

The weight ratio of polyvinyl acetate to polyvinylpyrrolidone in the polyvinyl acetate/polyvinylpyrrolidone mixture can be a wide range of values. Preferably, such ratio is between about 6.4 and 9:1; more likely between about 7:3 and 6:1, even more preferably about 8:2.

The molecular weight of the polyvinyl acetate component in the polyvinyl acetate/polyvinylpyrrolidone mixture can be a wide range of values. Preferably, the average molecular weight of the polyvinyl acetate is about 100 to about 10,000,000; or about 1,000 to about 1,000,000; or about 10,000 to about 1,000,000; or about 100,000 to about 1,000,000; or about 450,000.

The molecular weight of the polyvinylpyrrolidone component in the polyvinyl acetate/polyvinylpyrrolidone mixture can be a wide range of values. The average molecular weight of the polyvinylpyrrolidone can be from about 100 to about 10,000,000; or about 1,000 to about 1,000,000; or about 5,000 to about 500,000; or about 10,000 to about 100,000; or about 50,000.

The polyvinyl acetate and polyvinylpyrrolidone mixture can be prepared by a variety of processes including simply mixing powders of polyvinylpyrrolidone and polyvinyl acetate. In a preferred embodiment, such mixture is spray dried powder of a colloidal dispersion of polyvinyl acetate and polyvinylpyrrolidone solution. Optionally, sodium lauryl sulfate is used as a stabilizer in order to prevent agglomeration during spray drying process and/or colloidal silica is used to improve the flow properties of the polyvinyl acetate/polyvinylpyrrolidone mixture. Optionally, polyvinyl acetate and polyvinylpyrrolidone can be formed in a random or a block copolymer.

Optional Components

Suitable binding agents for the present invention include, but are not limited to, plant extracts, gums, synthetic or natural polysaccharides, polypeptides, alginates, synthetic polymers, or a mixture thereof.

Suitable plant extracts to be used as gelling agents include, but are not limited to, agar, ispaghula, psyllium, cydonia, ceratonia or a mixture thereof.

Suitable gums to be used as gelling agents include, but are not limited to, xanthan gum, guar gum, acacia gum, ghatti gum, karaya gum, tragacanth gum or a mixture thereof.

Suitable synthetics or natural hydrophilic polysaccharides to be used as gelling agents include, but are not limited to, hydroxyalkylcelluloses, cellulose ethers, cellulose esters, nitrocelluloses, dextrin, agar, carrageenan, pectin, furcellaran, starch or starch derivatives, cross-linked high amylose starch, or a mixture thereof.

Suitable polypeptides to be used as gelling agents include, but are not limited to, gelatin, collagen, polygeline or a mixture thereof.

Suitable alginates to be used as gelling agents include, but are not limited to, alginic acid, propylene glycol alginate, sodium alginate or a mixture thereof.

Suitable synthetic polymers to be used as gelling agents include, but are not limited to, carboxyvinyl polymer, polyvinyl alcohol, polyvinyl pyrrolidone, polyethelene oxide, polyethylene glycols, copolymers of ethylene oxide and propylene oxide and their copolymers or a mixture thereof.

In a preferred embodiment, the gelling agent is a gum such as xanthan gum, guar gum, acacia gum, ghatti gum, karaya gum, tragacanth gum or a mixture thereof, PEO 7,000,000 and HPMC K100 M.

In a most preferred embodiment, the gelling agent is xanthan gum.

Active Agent of the Coat

A suitable active pharmaceutical ingredient of the present invention is any active agent that it is desired to be delivered in a sustained-release dosage form. A comprehensive list of suitable pharmaceutical agents can be found in *The Merck Index*, 12$^{th}$ Ed. Preferably, the pharmaceutical agent is, but not limited to, isonicotinic acid hydrazide, sodium salicylate, pseudoephedrine hydrochloride, pseudoephedrine sulfate, acetaminophen or diclofenac sodium, verapamil, glipizide, nifedipine, felodipine, betahistine, albuterol, acrivastine, omeprazole, misoprostol, Tramadol®, oxybutynin, trimebutine, ciprofloxacin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisal, naproxen, ketorolac, diclofenac, tolmetin, sulindac, phenacetin, piroxicam, mefamanic acid, dextromethorphan, other non-steroidal anti-inflammatory drugs including salicylates, pharmaceutically acceptable salts thereof or mixtures thereof.

The solubility of the pharmaceutical agent in aqueous solution can be a wide variety of values. The aqueous solubility of the pharmaceutical agent can be less than $10^{-3}$ g/L, more than $10^{-3}$ g/L, more than $10^{-2}$ g/L, more than $10^{-1}$ g/L, more than 1 g/L, more than 10 g/L, more than 100 g/L, more than 500 g/L, more than 1000 g/L, or more than 2000 g/L. Preferably, the solubility is more than 100 g/L. More preferably, the solubility is more than 500 g/L, or even 1000 g/L.

The pharmaceutical agent can meet a variety of dosage requirements. For example, the dosage requirement of the pharmaceutical agent can be less than 1 mg/dosage unit, more than 1 mg/dosage unit, more than 10 mg/dosage unit, more than 100 mg/dosage unit, more than 200 mg/dosage unit, more than 300 mg/dosage unit, more than 400 mg/dosage unit, more than 500 mg/dosage unit, or more than 1000 mg/dosage unit. Preferably, the pharmaceutical agent is more than 50 mg/dosage unit. More preferably, the pharmaceutical agent is more than 100 mg/dosage unit. Most preferably, the pharmaceutical agent is more than 200 mg/dosage unit.

The coat can be between about 5% and about 90% by weight active pharmaceutical ingredient, or between about 5% and about 80% by weight api, or between about 10% and about 70% by weight api, or between about 10% and about 60% by weight api, or between about 15% and about 50% by weight api, or between about 15% and about 45% by weight api, or between about 15% and about 40% by weight api, or between about 20% and about 35% by weight api, or between about 20% and about 30% by weight api.

In particular embodiments, described further below, the weight of tramadol from a 100 mg tramadol tablet is about 21% by weight of the coat. The weight of tramadol from a 200 mg tablet is about 31% by weight of the coat. The weight of tramadol from a 300 mg tablet is about 30% by weight of the coat.

Routes of Administration

The tablet composition of the present invention can be administered through, but not limited to, a number of routes such as oral, sublingual, and rectal. The preferred route of administration of the compositions of the present invention is oral.

Compositions of the present invention that are suitable for oral administration may be presented as discrete units such as tablets or granules. Preferably, the compositions of the present invention are presented in a tablet form. Such tablets may be conventionally formed by compression or molding. Compressed tablets may be prepared by compressing in a suitable machine the mixture of one or more components described above. Molded tablets may be made by molding in a suitable machine the above components, which can be optionally moistened with an inert liquid diluent. The tablets may optionally be coated and/or have other identifying indicia visible to the consumer. A tablet can also be in a variety of forms, e.g., uncoated, dry coated, or film coated, etc. A tablet can also be in a variety of shapes (e.g., oval, sphere, etc.) and sizes A comprehensive discussion of tablets can be found in references such as *The Theory and Practice of Industrial Pharmacy* by Lachman et al., 3$^{rd}$ Ed. (Lea & Febiger, 1986).

Dissolution Profile of Sustained-Release Composition

The active agent of the composition exhibits the following in vitro dissolution profile when measured with a USP Type I apparatus in 50 mM phosphate, pH 6.8, and stirring between 50 and 150 rpm:

an average rate of between 10% and 30% per hour of the agent is released between 0 and 2 hours when tested in vitro using a USP Type I apparatus in 50 mM phosphate, pH 6.8, and stirring between 50 and 150 rpm; or between 10% and 40% of the agent is released from the formulation between 0 and about 2 hours of measurement, between about 30% and 60% of the agent is released from the formulation between 2 and about 7 hours of the measurement, between about 50% and 80% of the agent is released from the formulation between 7 and about 12 hours of measurement, and between about 80% and 100% of the agent is released from the formulation after about 20 hours of measurement; or more preferably between 15% and 35% of the agent is released from the formulation between at 2 hours of measurement, between about 40% and 60% of the agent is released from the formulation between at 7 hours of the measurement, between about 60% and 80% of the agent is released from the formulation at 12 hours of measurement, and between about 85% and 100% of the agent is released from the formulation after about 20 hours of measurement, or between 20% and 40% of the agent is released from the formulation between at 2 hours of measurement, between about 40% and 60% of the agent is released from the formulation between at 7 hours of the measurement, between about 60% and 80% of the agent is released from the formulation at 12 hours of measurement, and between about 85% and 100% of the agent is released from the formulation after about 20 hours of measurement.

The present invention will be more readily understood by referring to the following examples which are given to illustrate the invention rather than to limit its scope.

EXAMPLES

The cross-linked high amylose starch used in the these examples is made by a process comprising the steps of crosslinking and chemically modifying, followed by gelatinization and drying. Such process is described in more detail in U.S. Pat. No. 6,607,748 (Lenaerts et al.), which issued Aug. 19, 2003, and known in the marketplace under the name Contramid®. and described in Examples 1 and 2.

Example 1

A. Cross-Linking

High amylose starch (30.0 kg) containing about 70% wow of amylose (CI AmyloGel 03003) is placed in a reactor. To this reactor is added water (55.01) containing sodium hydroxide (30.0 g) and sodium sulfate (2.40 kg). The resulting slurry is heated to a temperature of 30° C. Phosphorus oxychloride (22.5 g) is added to the reaction mixture which is reacted for one hour.

B. Chemical Modification, Hydroxypropylation

The crude reaction mixture from Part A is transferred into a hydroxypropylation reactor. The reaction mixture is heated to 40° C. over 30 minutes and the reaction is purged with nitrogen. After a full purge, propylene oxide (1.80 kg) is added. The reaction mixture is kept at 40° C. for 20 hours. The reaction mixture is neutralized with 0.1 N $H_2SO_4$ (1:2 v/v) to a pH of 5.5. The starch slurry is washed with a basket-centrifuge at a speed of 1200 rpm. The obtained starch cake is re-slurrified in 35 l of water and centrifuged a second time. The resulting starch cake is dried in a flash dryer at an inlet temperature of 160° C. and an outlet temperature of 60° C.

C. Gelatinization

The modified granular starch cake is diluted in demineralized water in order to form a slurry at a concentration of about 8% calculated on dry substance The resulting slurry has a relative density of 1.032 kg/l compared to water. The pH of the modified starch slurry is adjusted to 6.0. The slurry is then heated to 160° C. by direct steam injection (Schlick Model 825). The temperature variation is not higher than ±1° C. The slurry is held in a holding column for a period of 4 minutes at a temperature of 160° C. and a pressure of about 5.5 bar. The pressure is then reduced to atmospheric by passing through a flash. The slurry is then contained at 95° C. in a hold tank.

D. Spray-Drying

The drying of the slurry from Part C is carried out using a Niro FSD 4 spray-drying tower equipped with a 0.8 mm nozzle and fed at 10 l/hour. The inlet temperature is fixed at 300° C. and the outlet temperature of 120° C. The obtained powder is a controlled release excipient with the following properties:

| Properties | |
|---|---|
| Moisture Content | 4.5% |
| Bulk Density | 150 g/l |
| Packed Density | 210 g/l |
| pH | 5.4 |
| Particle Size Peak Value (Laser Particle Sizer-Sympatec) | 50 μm |

Example 2

A. Cross-Linking

High amylose starch (30.0 kg) containing about 70% w/w of amylose (CI AmyloGel 03003) is placed in a reactor. To this reactor is added water (55.01) containing sodium hydroxide (30.0 g) and sodium sulfate (2.40 kg). The resulting slurry is heated to a temperature of 30° C. Sodium trimetaphosphate (45 g) is added to the reaction mixture which is reacted for one hour.

B. Chemical Modification, Hydroxypropylation

The crude reaction mixture from Part A is transferred into a hydroxypropylation reactor. The reaction mixture is heated to 40° C. over 30 minutes and the reaction is purged with nitrogen. After a full purge, propylene oxide (1.80 kg) is added. The reaction mixture is kept at 40° C. for 20 hours. The reaction mixture is neutralized with 0.1 N $H_2SO_4$ (1:2 v/v) to a pH of 5.5. The starch slurry is washed with a basket-centrifuge at a speed of 1200 rpm. The obtained starch cake is re-slurrified in 35 l of water and centrifuged a second time. The resulting starch cake is dried in a flash dryer at an inlet temperature of 160° C. and an outlet temperature of 60° C.

C. Gelatinization

The modified granular starch cake is diluted in demineralized water in order to form a slurry at a concentration of about 8% calculated on dry substance. The resulting slurry has a relative density of 1.032 kg/l compared to water. The pH of the modified starch slurry is adjusted to 6.0. The slurry is heated to 160° C. by direct steam injection (Schlick Model 825). The temperature variation is not higher than ±1° C. The slurry is held in a holding column for a period of 4 minutes at a temperature of 160° C. and a pressure of about 5.5 bar. The pressure is then reduced to atmospheric by passing through a flash. The slurry is then contained at 95° C. in a hold tank.

D. Spray-Drying

The slurry from Part C is carried out using a Niro FSD 4 spray-drying tower equipped with a 0.8 mm nozzle and fed at 10 l/hour The inlet temperature is fixed at 300° C. and the outlet temperature of 120° C. The obtained powder is a controlled release excipient with the following properties:

| Properties | |
|---|---|
| Moisture Content | 5.2% |
| Bulk Density | 103 g/l |
| Packed Density | 155 g/l |
| pH | 5.3 |
| Particle Size Peak Value (Laser Particle Sizer-Sympatec) | 70 μm |

Lubritab® is a product sold by Penwest Pharmaceuticals Co. (Cedar Rapids, Iowa, USA). Kollidon™ SR is a product produced by BASF (Germany). Encompress™ is a dicalcium phosphate dehydrate which can be purchased from Mendell (Patterson, N.Y.). Tramadol hydrochloride can be obtained from Chemagis Ltd., 3 Hashlosha Street, P.O. Box 9091, 61090, Tel Aviv, Israel. Methods of synthesis and purification of tramadol are described in, for example, U.S. Pat. Nos. 3,652,589, 5,414,129, 5,672,755, 5,874,620, 5,877,351, and 6,169,205.

Manufacturing Procedure

Tablets of the invention can be manufactured according to the process set out generally in the flow chart of FIG. 1, and described in more detail below.

Weighing: Raw materials are dispensed into clearly labeled containers,

Core Pre-Blend: Blend a portion of the Contramid® and Colloidal Silicon Dioxide and pass through #30 mesh screen into a suitable container.

Core Blend: Place a portion of the Contramid® into a blender Pass Tramadol Hydrochloride through a #30 mesh screen and add to blender. Rinse container with a portion of Contramid® and add to blender. Sieve Hydrogenated Vegetable Oil Type I through a #30 mesh screen and add to the blender. Add the Core Pre-Blend into the blender. Add the remaining Contramid® into the blender, and blend all ingredients. Sieve the Magnesium Stearate through a #30 mesh screen and add blend with other ingredients. Dispense blend in suitable container and identify as Core Blend.

Dry Coated Pre-Blend: Blend a portion of the Xanthan Gum and all of the Colloidal Silicon Dioxide and pass through #30 mesh screen.

Dry Coated Blend: Place a portion of the Kollidon® SR into a blender. Pass Tramadol Hydrochloride through Kason Separator with a #30 mesh screen into suitable container and add to blender. Rinse container with remaining xanthan gum and add to blender. Sieve Hydrogenated Vegetable Oil Type 1 through a #30 mesh screen and add to the blender. Place Dry Coated Pre-Blend and the remainder of the Kollidon® SR into the blender, and blend with all ingredients. Sieve the magnesium stearate through a #30 mesh screen and blend with other ingredients. Dispense granulation in suitable container and identify as Dry Coated Blend.

Compression: Use a Manesty Dry-Cota press to produce compression-coated tablets.

Example 3

Formulations A, B, and C, as shown in Table 1, were manufactured according to the process set out above.

TABLE 1

Recipes for Controlled Released Tramadol Formulations A, B and C.

| | Formulation A | | Formulation B | | Formulation C | |
| --- | --- | --- | --- | --- | --- | --- |
| | % | mg/tablet | % | mg/tablet | % | mg/tablet |
| 1) INGREDIENT Core | | | | | | |
| Tramadol Hydrochloride | 50 | 45 | 50 | 90 | 63.25 | 151.8 |
| Contramid ® | 48.3 | 43.47 | 48.3 | 86.94 | 35.05 | 84.1 |
| Hydrogenated Vegetable Oil | 0.75 | 0.675 | 0.75 | 1.35 | 0.75 | 1.8 |
| Silica | 0.2 | 0.18 | 0.2 | 0.36 | 0.20 | 0.5 |
| Magnesium Stearate | 0.75 | 0.675 | 0.75 | 1.35 | 0.75 | 1.8 |
| Core Total Weight | 100 | 90 | 100 | 180 | 100 | 240 |
| 2) COAT | | | | | | |
| Tramadol Hydrochloride | 21.15 | 55 | 30.56 | 110 | 30.56 | 148.5 |
| Silica | 0.20 | 0.52 | 0.20 | 0.72 | 0.20 | 1.0 |
| Kollidon SR ® | 51.42 | 133.7 | 45.16 | 162.58 | 45.16 | 219 |
| Xanthan Gum | 25.72 | 66.86 | 22.58 | 81.3 | 22.58 | 109.5 |
| Hydrogenated Vegetable Oil | 1.00 | 2.6 | 1.00 | 3.6 | 1.00 | 4.9 |
| Magnesium Stearate | 0.50 | 1.3 | 0.50 | 1.8 | 0.50 | 2.4 |
| Coat Total Weight | 100 | 260 | 100.00 | 360 | 100 | 485 |
| 3) COATED TABLET | | | | | | |
| Tramadol Hydrochloride | 28.57 | 100 | 37.04 | 200 | 41.38 | 300 |
| Contramid ® | 12.42 | 43.47 | 16.10 | 86.94 | 11.60 | 84.1 |
| Hydrogenated Vegetable Oil | 0.94 | 3.275 | 0.92 | 4.95 | 0.92 | 6.7 |
| Silica | 0.20 | 0.7 | 0.20 | 1.08 | 0.20 | 1.5 |
| Magnesium Stearate | 0.56 | 1.975 | 0.58 | 3.15 | 0.58 | 4.2 |
| Kollidon SR ® | 38.20 | 133.7 | 30.11 | 162.58 | 30.21 | 219 |
| Xanthan Gum | 19.11 | 66.86 | 15.06 | 81.3 | 15.10 | 109.5 |
| Coated Tablet TotalWeight: | 100 | 350 | 100 | 540 | 100 | 725 |

Figure 2:
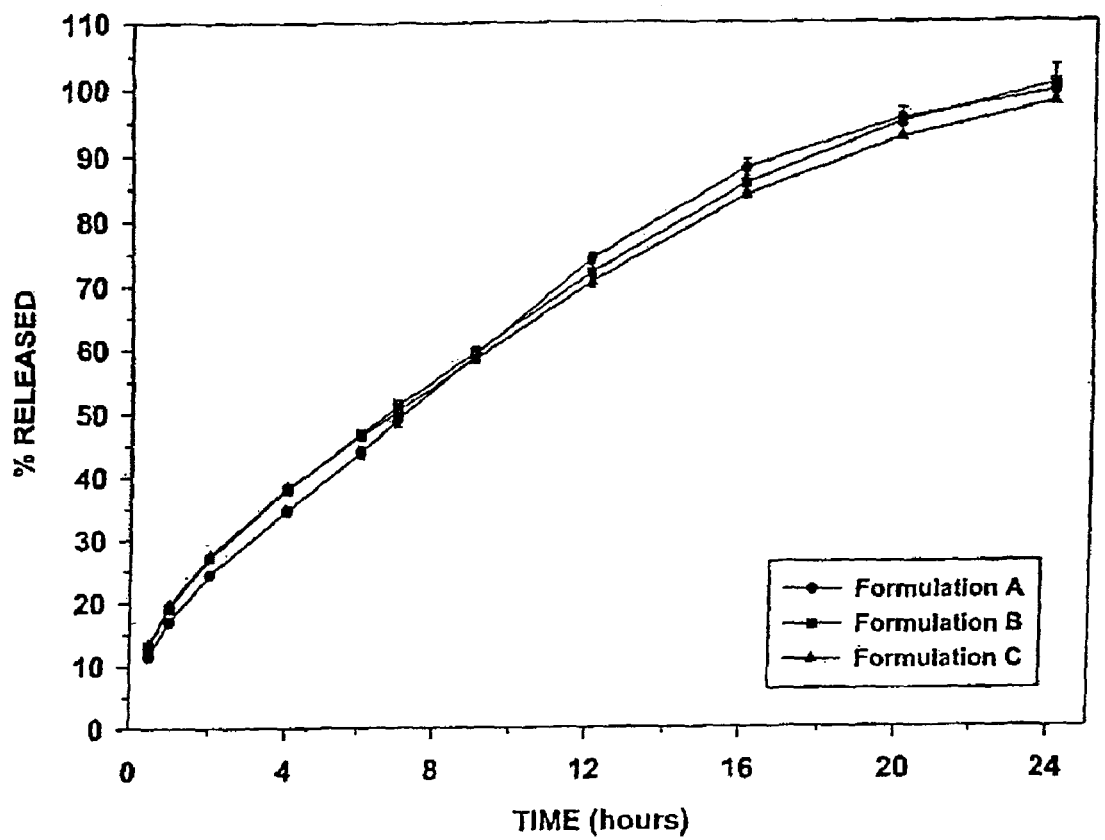
FIG. 2: Dissolution profiles of formulations A, B and C: In vitro performance of formulations A, B and C under USP Type 1 Conditions; sodium phosphate buffer, 50 mM, pH 6.8, 100 rpm. 6 tablets were tested per tire point.

Dissolution profiles of formulations A, B and C are shown in FIG. 2.

Tramadol Once Daily Formulation

The present invention relates to a controlled release tablet composition which provides analgesic effect within 2 hours of oral administration and lasts for at least 24 hours after administration.

The 200 mg dose of the inventive controlled release composition surprisingly provides a rapid onset of analgesic effect within 2 hours after oral administration, and a mean tramadol plasma concentration between 100 ng/mL and 200 ng/mL for at least 24 hours after a single dose.

Furthermore, at steady-state, the mean tramadol plasma concentration remains between 100 ng/mL and 350 ng/mL. The inventive controlled release compositions have surprisingly been shown to provide full clinical effect for at least 24 hours after oral administration Bioavailability Studies An object of the present invention is to provide flexible dosing options for patients with different analgesic requirements, with a once daily formulation.

One embodiment of the present invention is to provide a once daily formulation which upon initial ingestion of a dose of 100 mg would provide the desired early onset of action but achieve mean tramadol plasma concentrations of at least 45 ng/mL between 2 and 24 hours.

A further embodiment of the present invention is to provide a once daily formulation which upon initial ingestion of a dose of 200 mg would provide the desired early onset of action but achieve mean tramadol plasma concentrations of at least 100 ng/mL between 2 and 24 hours.

A further embodiment of the present invention is to provide a once daily formulation which upon initial ingestion of a dose of 300 mg would provide the desired early onset of action but achieve mean tramadol plasma concentrations of at least 150 ng/mL between 2 and 24 hours A further embodiment of the present invention is to provide a once daily formulation which upon initial ingestion of a dose of 400 mg would provide the desired early onset of action but achieve mean tramadol plasma concentrations of at least 180 ng/mL between 2 and 24 hours.

further embodiment of the present invention is to provide a once daily formulation which upon initial ingestion of a dose would provide a $C'_{max}$ to dose ratio of from about 0.90 to about 1.0.

A further embodiment of the present invention is to provide a once daily formulation which upon initial ingestion of a dose would provide a tramadol plasma concentration which rises steadily until peak tramadol concentrations are attained at a $T_{max}$ of about 4 hours to about 6 hours. Preferably, the $T_{max}$ occurs at about 5 hours to about 5.5 hours.

A further embodiment of the present invention is to provide a once daily formulation which upon initial ingestion of a dose would provide a tramadol plasma concentration which, after $T_{max}$, declines in a slow but steady manner, reflecting continuing absorption in addition to elimination processes. Preferably, the decline in the tramadol plasma concentration after $T_{max}$ occurs in a log-linear fashion with a mean apparent terminal elimination half-life of between about 5.5 hours and about 6.5 hours.

A further embodiment of the present invention is to provide a once daily formulation which upon initial ingestion of a dose would provide a tramadol plasma concentration which, after $T_{max}$, declines in a slow but steady manner, reflecting continuing absorption in addition to elimination processes, and which absorption continues for at least 20 hours from the time when absorption of the ingested dose begins.

A further embodiment of the present invention is to provide a once daily formulation which upon initial ingestion of a dose provides a tramadol plasma concentration which, after $T_{max}$, declines in a log-linear fashion with an apparent terminal elimination rate constant ($\lambda_z$) of about 0.12 h$^{-1}$.

A further embodiment of the present invention is to provide a once daily formulation which upon initial ingestion of a dose would provide a mean residence time (MRT) of tramadol ranging from about 15 hours to about 18 hours.

A further embodiment of the present invention is to provide a once daily formulation which upon initial ingestion of a dose would provide a half value duration (HVD) of tramadol which ranges from about 22.5 hours to about 25.4 hours.

A further embodiment of the present invention is to provide a once daily formulation which upon initial ingestion of a dose would provide a $C'_{max}$ to $AUC_{0-\infty}$ ratio of from about 0.04 h$^{-1}$ to about 0.06 h$^{-1}$. Preferably, the $C'_{max}$ to $AUC_{0-\infty}$ ratio is from about 0.04 h$^{-1}$ to about 0.05 h$^{-1}$. The ratio $C'_{max}/AUC_{0-\infty}$ is used for evaluating the rate of drug absorption.

A further embodiment of the present invention is to provide a once daily formulation which upon initial ingestion of a dose would provide a mean $AUC_{0-24}$ with respect to the tramadol plasma concentration which increases proportionally with dose over the range of dosage strengths of 100 mg to 300 mg of the controlled release composition.

A further embodiment of the present invention is to provide a once daily formulation which upon initial ingestion of a dose of 100 mg would provide a mean $AUC_{0-Tmax}$ of from about 610 ng·h/mL to about 630 ng·h/mL.

A further embodiment of the present invention is to provide a once daily formulation which upon initial ingestion of a dose of 200 mg would provide a mean $AUC_{0-Tmax}$ of from about 910 ng·h/mL to about 920 ng·h/mL.

A further embodiment of the present invention is to provide a once daily formulation which upon initial ingestion of a dose of 300 mg would provide a mean $AUC_{0-Tmax}$ of from about 1570 ng·h/mL to about 1590 ng·h/mL.

A further embodiment of the present invention is to provide a once daily formulation which upon initial ingestion of a dose provides a mean ratio of $AUC_{0-24}/AUC_{0-\infty}$ of tramadol plasma concentration which ranges between about 70% and about 85%. Preferably, the mean ratio of $AUC_{0-24}/AUC_{0-\infty}$ of tramadol plasma concentration ranges between about 74% and about 80%. As a result, about 15% to about 30% of the administered dose is still circulating in the plasma 24 hours post-dose, depending on the dose administered.

A further embodiment of the present invention is to provide a once daily formulation which upon initial ingestion of a dose would provide a ratio of the $C'_{max}$ to the dose released to the blood plasma in the first 24 hours ($AUC_{0-24}/AUC_{0-\infty}$ multiplied by the dose) of from about 1.10 to about 1.35. Preferably the ratio is from about 1.15 to about 1.31.

A further embodiment of the present invention is to provide a once daily formulation which upon initial ingestion of a dose, would provide a ratio of the $C'_{max}/T_{max}$ to the dose administered of from about 0.10 to about 0.20. Preferably the ratio is from about 0.12 to about 0.19.

A further embodiment of the present invention is to provide a once daily formulation which upon initial ingestion of a dose would provide a slope in ng/ml-hr following the peak blood plasma concentration level, which does not exceed a factor of about 0.035 of the total dose administered in mg. Preferably, the factor is about 0.03.

Tramadol pharmacokinetic parameters of the controlled release composition are presented in Table 2.

TABLE 2

Summary of Tramadol Pharmacokinetic Parameters

| Formulation Strength (mg) | Dose (mg) | Descriptive Statistic | $C'_{max}$ (ng/mL) | $AUC_{0-\infty}$ (ng·h/mL) | $AUC_{0-Tmax}$ (ng·h/mL) | $C'_{max}/AUC_{0-\infty}$ (h$^{-1}$) | $\lambda_z$ (h$^{-1}$) | Rstart (h) | half-life (h) | MRT (h) | HVD (h) | $AUC_{0-24}$ (ng·h/mL) | $AUC_{0-24}/AUC_{0-\infty}$ (%) |
|---|---|---|---|---|---|---|---|---|---|---|---|---|---|
| 100 | 100 | Arith. mean | 91.03 | 2108 | 625 | 0.0442 | 0.118 | 21.2 | 6.11 | 16.03 | 22.5 | 1635 | 78.9 |
|  |  | SD | 26.83 | 731 | 471 | 0.0052 | 0.024 | 4.3 | 1.31 | 2.13 | 3.4 | 465 | 6.60 |
| 200 | 200 | Arith. mean | 196.55 | 4416 | 915 | 0.0455 | 0.118 | 22.9 | 6.11 | 16.46 | 23.5 | 3374 | 77.2 |
|  |  | SD | 58.33 | 1192 | 567 | 0.0108 | 0.025 | 5.0 | 1.26 | 2.28 | 4.5 | 860 | 8.1 |
| 300 | 300 | Arith. mean | 290.08 | 6741 | 1578 | 0.0432 | 0.115 | 24.8 | 6.30 | 17.60 | 25.4 | 4900 | 73.9 |
|  |  | SD | 147.16 | 2156 | 1338 | 0.0126 | 0.023 | 4.4 | 1.52 | 3.03 | 6.6 | 1544 | 10.1 |
| 200 | 400 | Arith. mean | 487.35 | 9332 | NC | 0.0544 | 0.120 | 21.1 | 6.11 | 15.33 | NC | 7471 | 80.0 |
|  |  | SD | 210.43 | 3767 | NC | 0.0198 | 0.027 | 6.5 | 1.53 | 2.83 | NC | 2887 | 10.1 |

NC—Not calculated

A further embodiment of the present invention is to provide a once daily formulation which upon initial ingestion of a dose would provide a ratio of the $C'_{max}$ calculated with respect to the blood plasma concentration of O-desmethyltramadol, to the dose of tramadol of from about 0.19 to about 0.22. Preferably the ratio is from about 0.20 to 0.21.

A further embodiment of the present invention is to provide a once daily formulation which upon initial ingestion of a dose would provide an O-desmethyltramadol plasma concentration which rises steadily until peak tramadol concentrations are attained at a $T_{max}$ of about 8 hours to about 16 hours.

A further embodiment of the present invention is to provide a once daily formulation which upon initial ingestion of a dose would provide an O-desmethyltramadol plasma concentration which, after $T_{max}$, declines in a slow but steady manner, reflecting continuing tramadol absorption and subsequent metabolite formation in addition to elimination processes. Preferably, the decline in the O-desmethyltramadol plasma concentration occurs in a log-linear fashion with a mean apparent terminal elimination half-life of between about 6.7 hours and about 8.1 hours.

A further embodiment of the present invention is to provide a once daily formulation which upon initial ingestion of a dose would provide the formation of metabolite for at least 18 hours.

A further embodiment of the present invention is to provide a once daily formulation which upon initial ingestion of a dose would, after $T_{max}$, provide a decline in the O-desmethyltramadol plasma concentration in a log-linear fashion with an apparent terminal elimination rate constant ($\lambda_z$) of about 0.1 h$^{-1}$.

A further embodiment of the present invention is to provide a once daily formulation which upon initial ingestion of a dose would provide a half value duration (HVD) of O-desmethyltramadol which ranges from about 25.6 hours to about 28.1 hours.

A further embodiment of the present invention is to provide a once daily formulation which upon initial ingestion of a dose would provide a $C'_{max}$ to $AUC_{0-\infty}$ ratio calculated with respect to the O-desmethyltramadol plasma concentration, of about 0.04 h$^{-1}$. The ratio $C'_{max}/AUC_{0-\infty}$ is used for evaluating the rate of metabolite formation.

A further embodiment of the present invention is to provide a once daily formulation which upon initial ingestion of a dose would provide a mean $AUC_{0-24}$ calculated with respect to the O-desmethyltramadol plasma concentration, which increases proportionally with dose over the range of dosage strengths of 100 mg to 300 mg of the controlled release composition.

A further embodiment of the present invention is to provide a once daily formulation which upon initial ingestion of a dose of 100 mg would provide a mean $AUC_{0-Tmax}$ with respect to the O-desmethyltramadol plasma concentration of from about 175 ng·h/mL to about 180 ng·h/mL.

A further embodiment of the present invention is to provide a once daily formulation which upon initial ingestion of a dose of 200 mg would provide a mean $AUC_{0-Tmax}$ with respect to the O-desmethyltramadol plasma concentration of from about 530 ng·h/mL to about 550 ng·h/mL.

A further embodiment of the present invention is to provide a once daily formulation which upon initial ingestion of a dose of 300 mg would provide a mean $AUC_{0-Tmax}$ with respect to the O-desmethyltramadol plasma concentration of from about 580 ng·h/mL to about 590 ng·h/mL.

A further embodiment of the present invention is to provide a once daily formulation which upon initial ingestion of a dose provides a mean ratio of $AUC_{0-24}/AUC_{0-\infty}$ of O-desmethyltramadol plasma concentration which ranges between about 65% and about 80%. Preferably, the mean ratio of $AUC_{0-24}/AUC_{0-\infty}$ of O-desmethyltramadol plasma concentration ranges between about 68% and about 75%. As a result, about 25% to about 32% of the active metabolite is still circulating in the plasma 24 hours post-dose.

A further embodiment of the present invention is to provide a once daily formulation which upon initial ingestion of a dose would provide a ratio of the $C'_{max}$ calculated with respect to the O-desmethyltramadol plasma concentration, to the O-desmethyltramadol blood plasma concentration in the first 24 hours ($AUC_{0-24}/AUC_{0-\infty}$ multiplied by the dose of tramadol) of from about 0.0025 to about 0.0035. Preferably the ratio is from about 0.0027 to about 0.0031.

O-desmethyltramadol pharmacokinetic parameters of the controlled release composition are presented in Table 3.

TABLE 3

Summary of O-desmethyltramadol Pharmacokinetic Parameters

| Formulation Strength (mg) | Dose (mg) | Descriptive Statistic | $C'_{max}$ (ng/mL) | $AUC_{0-\infty}$ (ng·h/mL) | $AUC_{0-Tmax}$ (ng·h/mL) | $C'_{max}/AUC_{0-\infty}$ ($h^{-1}$) | $\lambda_z$ ($h^{-1}$) | Rstart (h) | half-life (h) | HVD (h) | $AUC_{0-24}$ (ng·h/mL) | $AUC_{0-24}/AUC_{0-\infty}$ (%) |
|---|---|---|---|---|---|---|---|---|---|---|---|---|
| 100 | 100 | Arith. mean | 20.38 | 520 | 179 | 0.0394 | 0.106 | 23.1 | 6.96 | 25.6 | 380 | 72.5 |
|  |  | SD | 6.67 | 170 | 92 | 0.0054 | 0.256 | 4.2 | 1.91 | 2.9 | 123 | 7.69 |
| 200 | 200 | Arith. mean | 43.13 | 1080 | 540 | 0.0395 | 0.111 | 25.1 | 6.69 | 26.3 | 782 | 71.3 |
|  |  | SD | 16.53 | 328 | 164 | 0.0079 | 0.029 | 4.0 | 1.84 | 5.0 | 259 | 8.8 |
| 300 | 300 | Arith. mean | 59.88 | 1641 | 587 | 0.0374 | 0.102 | 25.8 | 7.36 | 28.1 | 1107 | 67.9 |
|  |  | SD | 19.19 | 538 | 312 | 0.0092 | 0.029 | 3.6 | 2.21 | 6.6 | 346 | 11.0 |
| 200 | 400 | Arith. mean | 114.34 | 2866 | NC | 0.0457 | 0.094 | 18.7 | 8.14 | NC | 1909 | 74.6 |
|  |  | SD | 46.39 | 773 | NC | 0.0147 | 0.028 | 5.5 | 2.98 | NC | 651 | 10.9 |

NC—Not calculated

Example 4

(i) Dose Proportionality

Single Dose

A bioavailability study was conducted to assess the dose-proportionality between three dosage strengths (100 mg, 200 mg and 300 mg). This study was conducted with a suitable washout period between each administration. The doses were taken by 27 healthy human volunteers under fasting conditions.

Figure 3:
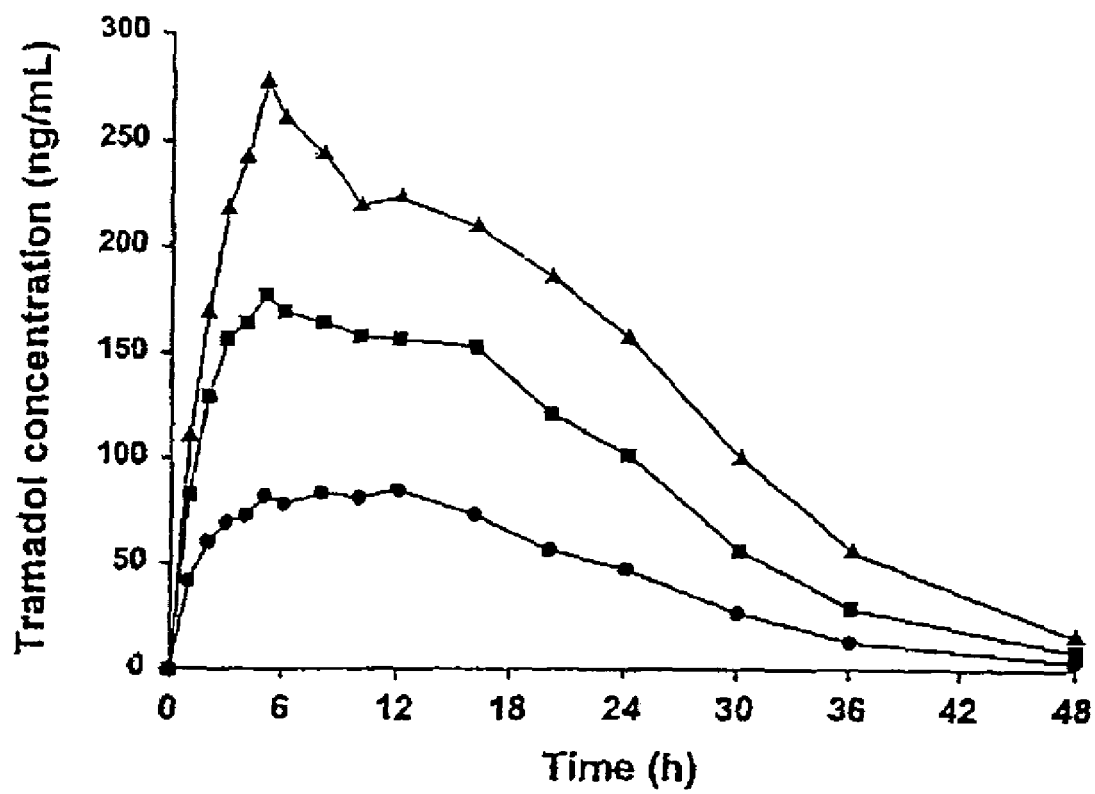
FIG. 3: Mean tramadol plasma concentrations following single-dose administration of (i) a 100 mg dose of the inventive controlled release composition (•), (ii) a 200 mg dose of the inventive controlled release composition (■), and (iii) a 300 mg dose of the inventive controlled release composition (▲).
Figure 4:
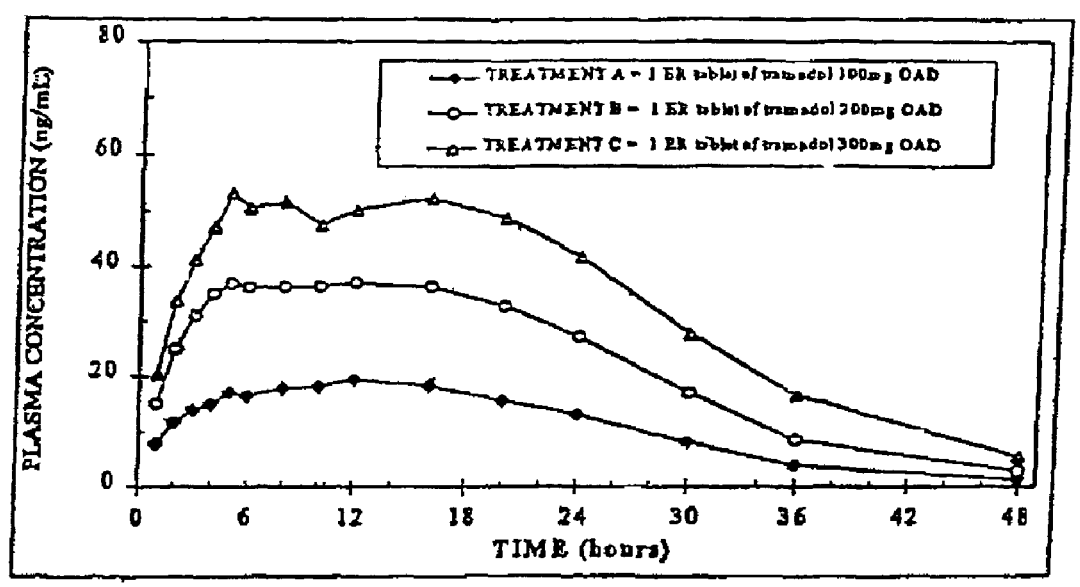
FIG. 4: Mean O-desmethyltramadol plasma concentrations of following single dose administration of either 100 mg (♦), 200 mg (○), and 300 mg (Δ) strength tramadol formulations (A, B, and C, respectively).

FIG. 3 depicts the mean plasma concentration time-profiles of tramadol obtained in the subjects after the administration of the inventive controlled release composition (dosed at 100 mg, 200 mg and 300 mg of tramadol HCl). The data used to create FIG. 3 is included in Table 4.

TABLE 4

Mean (±SD) Tramadol Plasma Concentrations (ng/mL)

| Time | 100 mg dose of the inventive controlled release composition | 200 mg dose of the inventive controlled release composition | 300 mg dose of the inventive controlled release composition |
|---|---|---|---|
| 0 | 0 | 0 | 0 |
| 1 | 41.8 ± 14.1 | 82.5 ± 24.1 | 110.2 ± 36.7 |
| 2 | 60.0 ± 14.6 | 129.2 ± 25.7 | 168.6 ± 52.1 |
| 3 | 69.2 ± 20.2 | 156.5 ± 37.0 | 218.1 ± 82.3 |
| 4 | 72.5 ± 21.8 | 164.0 ± 44.9 | 242.0 ± 96.2 |
| 5 | 81.7 ± 24.2 | 177.2 ± 61.8 | 277.1 ± 153.8 |
| 6 | 77.9 ± 24.7 | 169.2 ± 58.1 | 260.3 ± 134.8 |
| 8 | 83.0 ± 25.6 | 164.1 ± 52.7 | 243.6 ± 127.1 |
| 10 | 81.0 ± 24.7 | 157.8 ± 57.8 | 219.8 ± 101.6 |
| 12 | 84.4 ± 25.3 | 156.4 ± 55.9 | 223.4 ± 85.1 |
| 16 | 73.0 ± 24.1 | 152.8 ± 42.0 | 209.9 ± 70.2 |
| 20 | 56.4 ± 19.4 | 121.0 ± 34.4 | 185.7 ± 62.7 |
| 24 | 47.2 ± 20.9 | 101.6 ± 38.2 | 157.0 ± 60.4 |
| 30 | 26.8 ± 15.0 | 56.4 ± 28.3 | 99.9 ± 50.3 |
| 36 | 13.2 ± 9.4 | 29.1 ± 18.7 | 55.9 ± 37.9 |
| 48 | 3.7 ± 3.5 | 8.5 ± 6.7 | 15.7 ± 13.1 |

The results from this study indicated that the 100 mg, 200 mg and 300 mg formulations of the inventive controlled release composition are dose proportional with respect to the rate and extent of absorption of tramadol and the rate and extent of formation of O-desmethyltramadol.

Bioavailability studies were conducted in order to characterize the pharmacokinetic properties of the inventive controlled release composition and to demonstrate similar exposure of the drug and/or its active metabolite when compared to a reference product.

Example 5

(ii) Comparison to a Twice-Daily Formulation

Single Dose

The 2×200 mg dosage of the inventive controlled release composition was compared to the twice daily formulation Topalgic® LP (200 mg) tablets manufactured by Laboratoires Hoechst Houdé in a comparative bioavailability study after administration under fasting conditions in 24 healthy human volunteers.

The pharmacokinetic results from the inventive controlled release composition were compared to those obtained following twice daily administration (at 12-hour intervals) of the reference formulation in order to assess bioequivalence between the test and the reference product. Based on calculation of the 90% confidence interval of the test versus reference ratios of geometric means, the extent of exposure (determined by assessment of $AUC_{0-t}$ and $AUC_{0-\infty}$ of tramadol following dose normalization) was within the conventional bioequivalence interval of 80-125% for the log-transformed parameters. Thus the inventive controlled release composition and the twice daily formulation were found to be bioequivalent in terms of the overall exposure to tramadol. Results for tramadol $AUC_{0-\infty}$ are presented in Table 5.

TABLE 5

Comparison of $AUC_{0-\infty}$ (Simile-dose versus twice-daily formulation)

| Treatment | Arithmetic Mean ± SD (ng·h/mL) | Geometric Mean Ratio (90% Confidence Interval) |
|---|---|---|
| 2 × 200 mg dose of the inventive controlled release composition | 9332 ± 3767 | 103 (98-109) |
| 1 × 200 mg Topalgic ® LP BID | 8897 ± 3124 |  |

Figure 5:
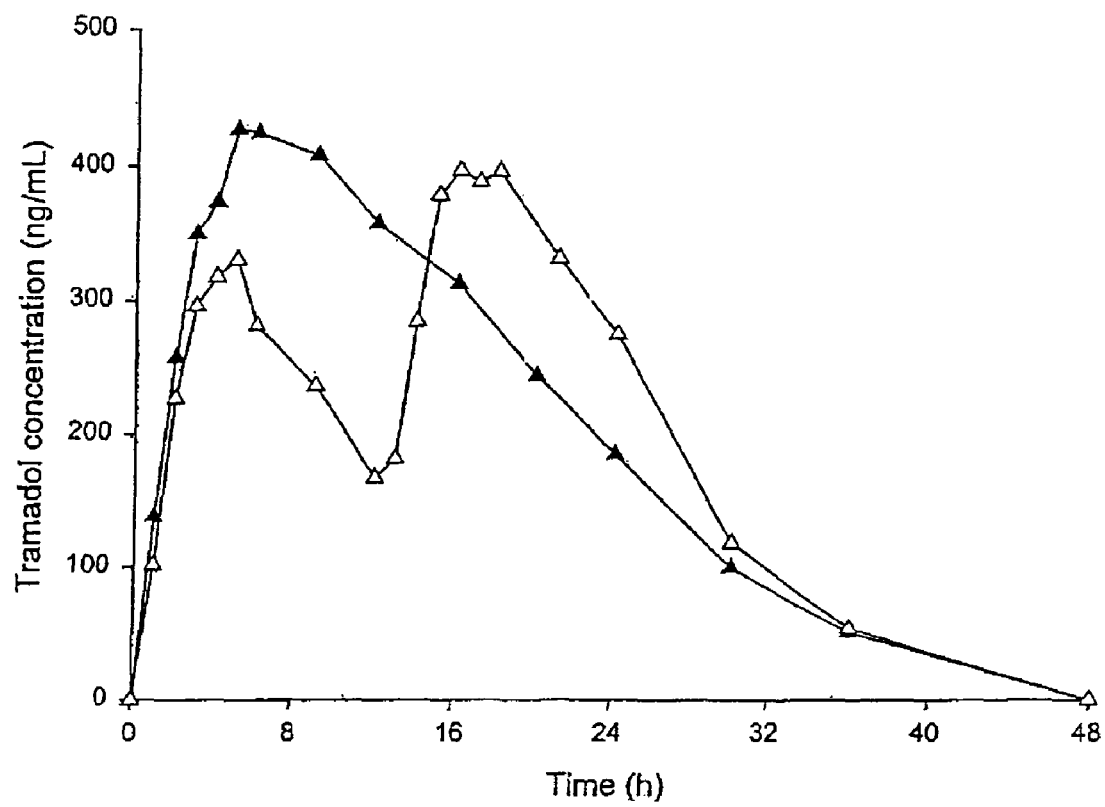
FIG. 5: Mean tramadol plasma concentrations following single-dose administration of (i) 2×200 mg doses of the inventive controlled release composition (▲); and (ii) Topalgic® LP 200 mg BID q12h (Δ).

FIG. 5 depicts the arithmetic mean plasma concentration time-course profiles of tramadol obtained after the administration of the inventive controlled release composition once a day and of the reference product in one day at 12-hour intervals in the 24 healthy volunteers. The data used to create FIG. 5 is included in Table 6.

TABLE 6

Mean Tramadol Plasma Concentrations (ng/mL)

| | Test formulation | | Reference formulation |
|---|---|---|---|
| Time | Conc. 2 × 200 mg dose of the inventive composition | Time | Conc. 200 mg BID |
| 0 | 0 | 0 | 0 |
| 1 | 138.49 ± 58.62 | 1 | 101.93 ± 43.72 |
| 2 | 257.56 ± 81.20 | 2 | 226.89 ± 72.90 |
| 3 | 350.21 ± 166.42 | 3 | 296.35 ± 99.46 |
| 4 | 373.93 ± 124.33 | 4 | 318.22 ± 91.27 |
| 5 | 427.66 ± 166.90 | 5 | 330.88 ± 98.68 |
| 6 | 424.72 ± 176.20 | 6 | 281.67 ± 85.95 |
| 9 | 408.61 ± 196.28 | 9 | 236.39 ± 87.89 |
| 12 | 357.88 ± 162.48 | 12 | 167.41 ± 65.49 |
| 16 | 312.70 ± 153.34 | 13 | 181.96 ± 70.51 |
| 20 | 243.94 ± 117.93 | 14 | 284.67 ± 126.76 |
| 24 | 184.96 ± 102.90 | 15 | 378.82 ± 136.23 |
| 30 | 99.78 ± 61.60 | 16 | 396.87 ± 146.56 |
| 36 | 51.01 ± 43.33 | 17 | 388.83 ± 142.32 |
| 48 | 0 | 18 | 396.38 ± 140.65 |
| | | 21 | 331.81 ± 121.52 |
| | | 24 | 275.00 ± 110.61 |
| | | 30 | 118.69 ± 64.92 |
| | | 36 | 54.04 ± 39.07 |
| | | 48 | 0 |

Figure 6:
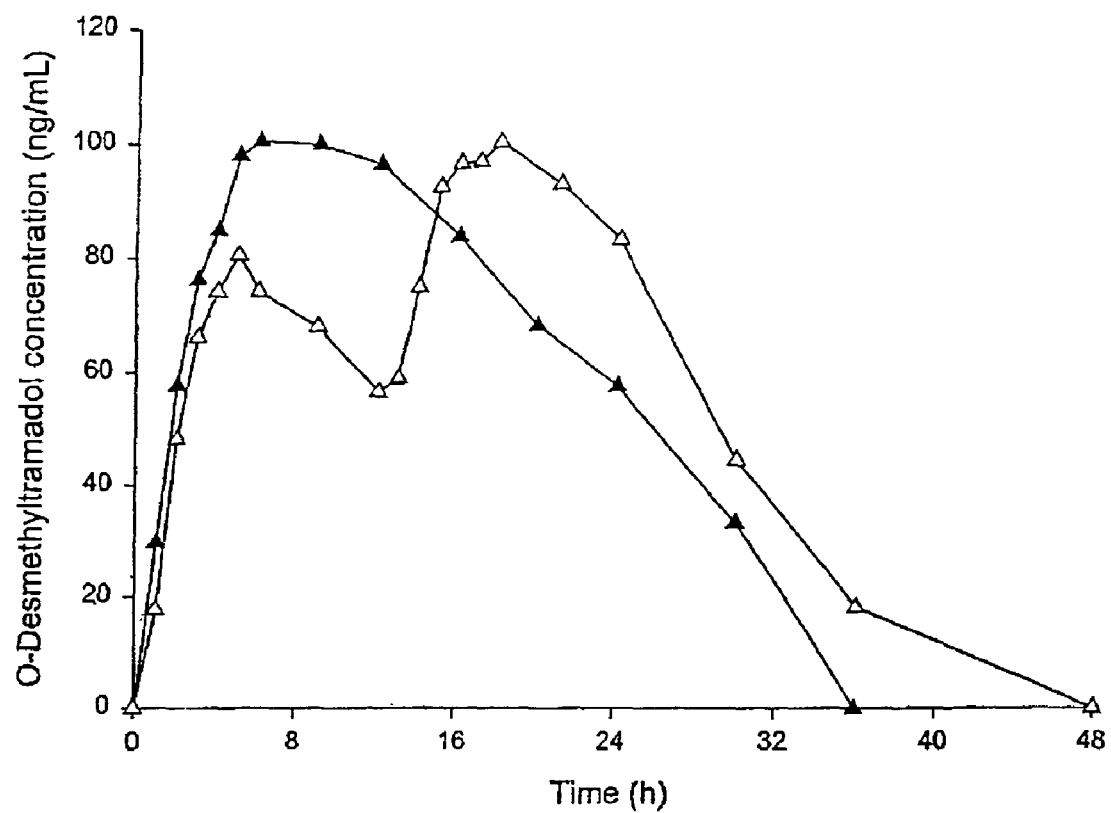
FIG. 6: Mean O-desmethyltramadol plasma concentrations following single-dose administration of (i) 2×200 mg doses of the inventive controlled release composition (▲); and (ii) Topalgic® LP 200 mg BID q12h (Δ).

FIG. 6 depicts the arithmetic mean plasma concentration time-course profiles of O-desmethyltramadol obtained after the administration of the inventive controlled release composition once-a-day and of the reference product in one day at 12-hour intervals in the 24 healthy volunteers. The data used to create FIG. 6 is included in Table 7.

TABLE 7

Mean (±SD) O-desmethyltramadol Plasma Concentrations (ng/mL)

| | Test formulation | | Reference formulation |
|---|---|---|---|
| Time | Conc. 2 × 200 mg dose of the inventive composition | Time | Conc. 200 mg BID |
| 0 | 0 | 0 | 0 |
| 1 | 29.82 ± 17.0 | 1 | 17.7 ± 14.6 |
| 2 | 57.8 ± 17.0 | 2 | 48.3 ± 17.5 |
| 3 | 76.3 ± 31.6 | 3 | 66.2 ± 25.9 |
| 4 | 84.9 ± 30.9 | 4 | 74.3 ± 26.2 |
| 5 | 98.0 ± 41.4 | 5 | 80.64 ± 29.2 |
| 6 | 100.6 ± 41.7 | 6 | 74.3 ± 26.1 |
| 9 | 99.9 ± 41.7 | 9 | 68.1 ± 24.6 |
| 12 | 96.52 ± 38.8 | 12 | 56.6 ± 22.1 |
| 16 | 83.9 ± 32.6 | 13 | 59.1 ± 23.8 |
| 20 | 68.2 ± 28.8 | 14 | 75.1 ± 32.6 |
| 24 | 57.6 ± 28.0 | 15 | 92.6 ± 38.0 |
| 30 | 33.2 ± 20.0 | 16 | 96.7 ± 37.0 |
| 36 | 0 | 17 | 97.0 ± 34.5 |
| 48 | 0 | 18 | 100.4 ± 33.6 |
| | | 21 | 93.0 ± 32.4 |
| | | 24 | 83.3 ± 37.8 |
| | | 30 | 44.4 ± 21.6 |
| | | 36 | 18.1 ± 16.8 |
| | | 48 | 0 |

Example 6

(iii) Comparison to a Twice Daily Formulation

Steady State

The 200 mg dosage of the inventive controlled release composition was compared to the twice daily formulation, Topalgic® LP (100 mg) tablets, manufactured by Laboratoires Hoechst Houdé, in a comparative bioavailability study after multiple administration under fasting conditions in 26 healthy human volunteers.

The results from this study indicated that the inventive controlled release composition is equivalent to the reference product with respect to the rate and extent of absorption of tramadol and the rate and extent of formation of O-desmethyltramadol. The comparative bioavailability of the two products was assessed on the basis of the confidence interval for the primary variable $AUC_{ss}$ for tramadol and O-desmethyltramadol in relation to the conventional bioequivalence range of 80% to 125%. Results for tramadol $AUC_{ss}$ are presented in Table 8.

TABLE 8

Comparison of $AUC_{ss}$ (Once-a-day versus twice-daily formulation)

| Treatment | Arithmetic Mean ± SD (ng · h/mL) | Geometric Mean Ratio (90% Confidence Interval) |
|---|---|---|
| 200 mg dose of the inventive controlled release composition | 5185 ± 1460 | 92.4 (87.5-97.5) |
| Topalgic ® LP 100 mg BID | 5538 ± 1214 | |

Figure 7:
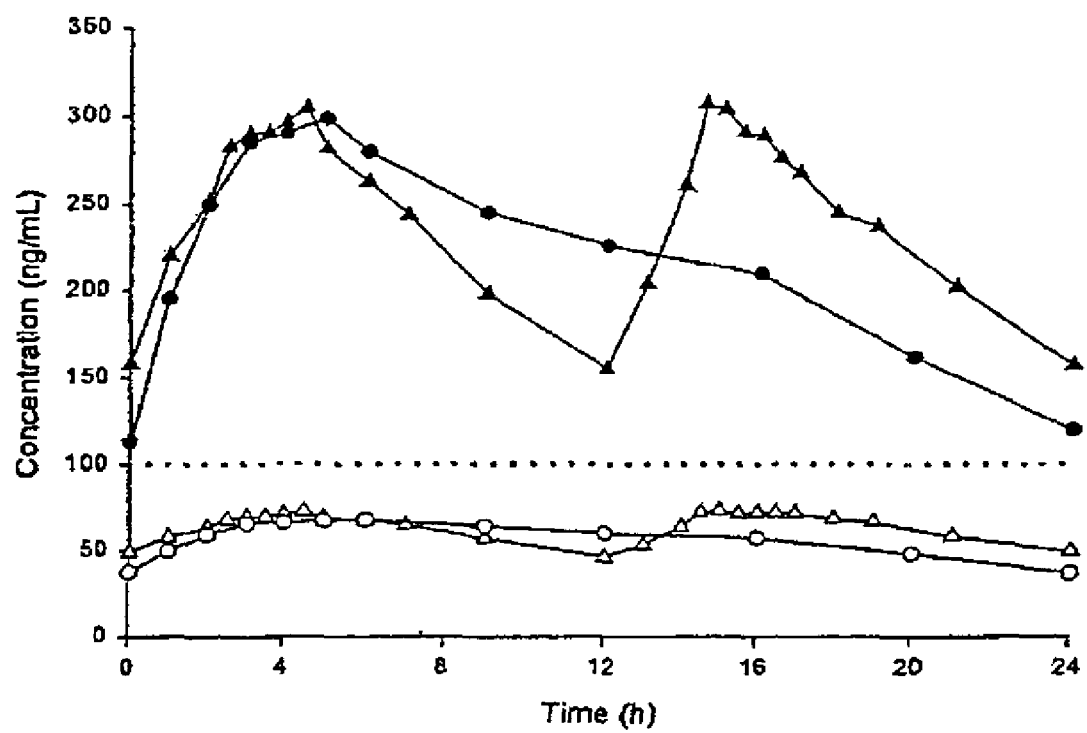
FIG. 7: Mean steady-state tramadol and O-desmethyltramadol plasma concentration following administration of (i) a 200 mg dose of the inventive controlled release composition (• & ○); and (ii) Topalgic® LP 100 mg BID q12h (▲ & Δ).

FIG. 7 depicts the arithmetic mean plasma concentration time-course profiles of tramadol and O-desmethyltramadol following administration of a 200 mg dose of the inventive controlled release composition once a day and of the reference product (Topalgic® LP 100 mg BID) in one day at 12 hour intervals. The data used to create FIG. 7 is included in Table 9.

TABLE 9

Mean (±SD) Tramadol and O-desmethyltramadol Plasma Concentrations (ng/mL)

| Test formulation (200 mg dose of the inventive controlled release composition) | | | Reference formulation (100 mg BID) | | |
|---|---|---|---|---|---|
| Time | Tramadol | Metabolite | Time | Tramadol | Metabolite |
| 0 | 113.3 ± 48.8 | 37.6 ± 9.0 | 0 | 157.8 ± 48.8 | 49.1 ± 10.7 |
| 1 | 195.4 ± 58.4 | 49.9 ± 13.9 | 1 | 220.2 ± 61.1 | 58.1 ± 12.9 |
| 2 | 249.5 ± 61.0 | 58.9 ± 14.4 | 2 | 251.6 ± 60.9 | 63.1 ± 14.6 |
| 3 | 285.0 ± 66.0 | 65.4 ± 16.3 | 2.5 | 282.7 ± 65.3 | 68.0 ± 14.7 |
| 4 | 290.6 ± 65.5 | 66.2 ± 16.0 | 3 | 290.8 ± 59.7 | 69.4 ± 15.6 |
| 5 | 298.9 ± 81.1 | 67.3 ± 16.7 | 3.5 | 290.9 ± 70.6 | 69.6 ± 15.7 |
| 6 | 280.0 ± 70.7 | 67.7 ± 17.5 | 4 | 297.3 ± 71.3 | 71.3 ± 15.3 |
| 9 | 244.9 ± 58.4 | 63.9 ± 16.8 | 4.5 | 305.2 ± 75.2 | 72.8 ± 15.6 |
| 12 | 226.0 ± 70.2 | 59.8 ± 17.2 | 5 | 281.8 ± 65.5 | 69.1 ± 15.7 |
| 16 | 209.4 ± 73.4 | 57.3 ± 14.8 | 6 | 262.8 ± 55.5 | 67.4 ± 17.3 |
| 20 | 161.5 ± 68.9 | 47.9 ± 12.1 | 7 | 243.9 ± 60.2 | 64.9 ± 15.2 |
| 24 | 119.9 ± 59.1 | 37.1 ± 8.9 | 9 | 198.0 ± 54.4 | 57.0 ± 12.8 |
| | | | 12 | 154.6 ± 47.8 | 46.2 ± 10.5 |
| | | | 13 | 203.5 ± 55.4 | 53.2 ± 12.8 |
| | | | 14 | 260.7 ± 54.2 | 63.7 ± 15.0 |
| | | | 14.5 | 307.2 ± 59.9 | 72.2 ± 16.5 |
| | | | 15 | 303.7 ± 60.5 | 73.2 ± 17.1 |
| | | | 15.5 | 290.7 ± 54.3 | 71.3 ± 16.8 |

TABLE 9-continued

Mean (±SD) Tramadol and O-desmethyltramadol
Plasma Concentrations (ng/mL)

| Test formulation (200 mg dose of the inventive controlled release composition) | | | Reference formulation (100 mg BID) | | |
|---|---|---|---|---|---|
| Time | Tramadol | Metabolite | Time | Tramadol | Metabolite |
| | | | 16 | 289.0 ± 54.6 | 72.1 ± 15.6 |
| | | | 16.5 | 276.4 ± 53.2 | 72.1 ± 16.8 |
| | | | 17 | 267.6 ± 55.2 | 71.6 ± 16.8 |
| | | | 18 | 244.6 ± 58.4 | 68.2 ± 15.0 |
| | | | 19 | 237.1 ± 59.4 | 66.4 ± 14.8 |
| | | | 21 | 201.5 ± 52.7 | 57.9 ± 12.0 |
| | | | 24 | 156.9 ± 49.9 | 49.6 ± 10.1 |

The present invention is not limited in scope by the specific embodiments disclosed in these examples which are intended to illustrate the most preferred embodiments of the invention. Indeed, various modifications of the invention or other embodiments which are functionally equivalent to those shown and described herein will become apparent to those skilled in the art and are intended to be covered by the appended claims.

A number of references have been cited, the entire disclosures of which are incorporated herein by reference.

Although various examples of combined elements of the invention have been described, it will also be understood that these are not intended to be exhaustive and features of one embodiment may be combined with those of another, and such other combinations are contemplated to be within the scope of the invention disclosed herein.

What is claimed is:

1. A once daily oral pharmaceutical composition for controlled release of tramadol, comprising:
a core comprising tramadol dispersed in a first controlled-release matrix comprising cross-linked high amylose starch, wherein the tramadol is present in the core in an amount from about 10 to about 70 weight-percent of the composition of the core, and
a compression coat formed over the core and comprising tramadol dispersed in a mixture of polyvinyl acetate and polyvinylpyrrolidone at a weight ratio of about 8:2 such that the mixture comprises from about 30% to about 65% by weight of the coat,
wherein the release of tramadol from the core is slower than the release of tramadol from the coat,
wherein the composition, upon initial administration of one dose, provides an onset of analgesic effect within 2 hours, which analgesic effect continues for at least 24 hours after administration, and wherein the composition is a tablet.

2. The composition of claim 1, wherein the composition comprises 200 mg of tramadol and upon initial administration of one dose, provides a mean plasma concentration of at least 100 ng/mL within 2 hours of administration and continues to provide a mean plasma concentration of at least 100 ng/mL for at least 22 hours after administration.

3. The composition of claim 2 which continues to provide a mean plasma concentration of at least 100 ng/mL for at least 23 hours after administration.

4. The composition of claim 2 which continues to provide a mean plasma concentration of at least 100 ng/mL for at least 24 hours after administration.

5. The composition of claim 1, comprising 100 mg of tramadol, wherein the composition, upon initial administration of one dose, provides a mean plasma concentration of at least 50 ng/mL within 2 hours of administration and continues to provide a mean plasma concentration of at least 50 ng/mL for at least 22 hours after administration.

6. The composition of claim 5, which continues to provide a mean plasma concentration of at least 50 ng/mL for at least 23 hours after administration.

7. The composition of claim 1 comprising 300 mg of tramadol, wherein the composition, upon initial administration of one dose, provides a mean plasma concentration of at least 150 ng/mL within 2 hours of administration and continues to provide a mean plasma concentration of at least 150 ng/mL for at least 22 hours after administration.

8. The composition of claim 7, which continues to provide a mean plasma concentration of at least 150 ng/mL for at least 23 hours after administration.

9. The composition of claim 7, which continues to provide a mean plasma concentration of at least 150 ng/mL for at least 24 hours after administration.

10. The composition of claim 1, comprising 200 mg of tramadol, wherein upon initial administration of 400 mg, the composition provides a mean plasma concentration of at least 200 ng/mL for at least 22 hours after administration.

11. The composition of claim 10, which upon said administration provides a mean plasma concentration of at least 190 ng/mL for at least 23 hours after administration.

12. The composition of claim 10, which upon said administration provides a mean plasma concentration of at least 180 ng/mL for at least 24 hours after administration.

13. The composition of claim 5, wherein the mean maximum plasma concentration ($C_{max}$) is less than 100 ng/mL.

14. The composition of claim 7, wherein the mean maximum plasma concentration ($C_{max}$) is less than 300 ng/mL.

15. The composition of claim 7, wherein the mean maximum plasma concentration ($C_{max}$) is less than two times the mean plasma concentration obtained 24 hours after administration ($C_{24h}$).

16. The composition of claim 10, wherein the mean maximum plasma concentration ($C_{max}$) is less than 2.3 times the mean plasma concentration obtained 24 hours after administration ($C_{24}$).

17. The composition of claim 1 comprising 100 mg of tramadol or a salt thereof, wherein the composition, upon initial administration of one dose, provides an O-desmethyltramadol mean plasma concentration of at least 11 ng/mL within 2 hours of administration and continues to provide an O-desmethyltramadol mean plasma concentration of at least 12 ng/mL for at least 24 hours after administration.

18. The composition of claim 17 comprising 200 mg of tramadol or a salt thereof, wherein the composition, upon initial administration of one dose, provides an O-desmethyltramadol mean plasma concentration of at least 24 ng/mL within 2 hours of administration and continues to provide an O-desmethyltramadol mean plasma concentration of at least 25 ng/mL for at least 24 hours after administration.

19. The composition of claim 17 comprising 300 mg of tramadol or a salt thereof, wherein the composition, upon initial administration of one dose, provides an O-desmethyltramadol mean plasma concentration of at least 32 ng/ml within 2 hours of administration and continues to provide an O-desmethyltramadol mean plasma concentration of at least 32 ng/mL for at least 24 hours after administration.

20. The composition of claim 18, wherein upon initial administration of 400 mg, the composition provides an O-desmethyltramadol mean plasma concentration of at least 50 ng/mL within 2 hours of administration and continues to provide an O-desmethyltramadol mean plasma concentration of at least 50 ng/mL for at least 24 hours after administration.

21. The composition of claim 1, wherein between 10% and 40% of the agent is released from the formulation between 0 and about 2 hours of measurement, between about 30% and 60% of the agent is released from the formulation between 2 and about 7 hours of the measurement, between about 50% and 80% of the agent is released from the formulation between 7 and about 12 hours of measurement, and between about 80% and 100% of the agent is released from the formulation after about 20 hours of measurement.

22. The composition of claim 1 having a dissolution rate in vitro when measured with HPLC-USP apparatus Type 1 at 100 rpm in 50 mM sodium phosphate buffer at pH 6.8, from about 5% to about 30% after 1 hour; from about 15% to about 40% after 2 hours; from about 20% to about 50% after 4 hours, from about 30% to about 70% after 8 hours; from about 40% to about 90% after 12 hours; from about 50% to about 100% after 16 hours; from 60% to about 100% after 24 hours.

23. The composition of claim 1 having a dissolution rate in vitro when measured with HPLC-USP apparatus Type 1 at 100 rpm in 50 mM sodium phosphate buffer at pH 6.8, from about 10% to about 25% after 1 hour; from about 15% to about 30% after 2 hours; from about 25% to about 40% after 4 hours, from about 40% to about 55% after 8 hours; from about 60% to about 75% after 12 hours; from about 70% to about 90% after 16 hours; from about 90% to about 100% after 24 hours.

24. The composition of claim 22, wherein the composition comprises 200 mg of tramadol.

25. The composition of claim 23, wherein the composition comprises 200 mg of tramadol.

26. The composition of claim 1, wherein the tramadol is present in the core in an amount from about 20 to about 60 weight-percent of the composition of the core.

27. The composition of claim 1, wherein the tramadol is present in the coat in an amount from about 15 to about 40 weight-percent of the composition of the coat.

28. The composition of claim 1, wherein the polyvinylacetate disposed in the coat has a molecular weight from about 100,000 to about 1,000,000.

29. The composition of claim 1, wherein the polyvinylpyrollidone in the coat has a molecular weight from about 10,000 to about 100,000.

* * * * *